United States Patent
Mora-Gutierrez et al.

(10) Patent No.: US 7,780,873 B2
(45) Date of Patent: *Aug. 24, 2010

(54) BIOACTIVE COMPLEXES COMPOSITIONS AND METHODS OF USE THEREOF

(75) Inventors: Adela Mora-Gutierrez, Houston, TX (US); Michael H. Gurin, Glenview, IL (US)

(73) Assignee: Texas A&M University System, College Station, TX (US)

( * ) Notice: Subject to any disclaimer, the term of this patent is extended or adjusted under 35 U.S.C. 154(b) by 660 days.

This patent is subject to a terminal disclaimer.

(21) Appl. No.: 11/530,635

(22) Filed: Sep. 11, 2006

(65) Prior Publication Data

US 2007/0085059 A1 Apr. 19, 2007

Related U.S. Application Data

(63) Continuation-in-part of application No. 10/784,842, filed on Feb. 23, 2004, now Pat. No. 7,118,688, and a continuation-in-part of application No. 11/306,582, filed on Jan. 3, 2006.

(51) Int. Cl.
*C09K 15/32* (2006.01)

(52) U.S. Cl. ............... 252/400.21; 252/400.22; 252/401; 252/402; 426/602; 426/604; 426/662; 426/631; 435/68.1; 435/272

(58) Field of Classification Search ............ 252/400.21, 252/400.22, 401, 402; 426/602, 604, 631, 426/662, 99; 435/272, 68.1; 424/405, 486, 424/401, 94.1, 491; 428/402.21; 514/12
See application file for complete search history.

(56) References Cited

U.S. PATENT DOCUMENTS

| 4,668,771 | A | * | 5/1987 | Kawakami et al. ......... 530/366 |
| 4,898,780 | A | | 2/1990 | Seitz |
| 4,963,385 | A | * | 10/1990 | Antrim et al. ............... 426/602 |
| 5,552,167 | A | | 9/1996 | Taylor et al. |
| 5,650,190 | A | | 7/1997 | Buikstra et al. |
| 5,834,427 | A | * | 11/1998 | Han et al. ...................... 514/12 |
| 6,200,609 | B1 | * | 3/2001 | Meister et al. ................ 426/61 |
| 6,916,490 | B1 | * | 7/2005 | Garver et al. ............... 424/489 |
| 7,041,324 | B2 | * | 5/2006 | Myhre ......................... 426/72 |
| 2003/0059474 | A1 | | 3/2003 | Scott et al. |
| 2003/0110951 | A1 | * | 6/2003 | Tyler et al. .................... 99/275 |
| 2003/0144356 | A1 | * | 7/2003 | Goodale ..................... 514/560 |
| 2003/0228339 | A1 | | 12/2003 | El-Nokaly et al. |
| 2004/0043013 | A1 | | 3/2004 | McCleary |
| 2004/0120984 | A1 | * | 6/2004 | Artiss et al. ................. 424/439 |
| 2004/0151750 | A1 | | 8/2004 | O'Leary et al. |
| 2004/0247683 | A1 | | 12/2004 | Popescu et al. |
| 2005/0048088 | A1 | * | 3/2005 | Zulli et al. .................. 424/401 |
| 2005/0238790 | A1 | * | 10/2005 | Ishimoto et al. ............. 426/656 |

OTHER PUBLICATIONS

Cavamax CoQ10, The highly bioavailble coenzyme Q10 powder, http://www.wacker.com/cms/media/publications/downloads/6201_EN.pdf.*

* cited by examiner

*Primary Examiner*—Ling-Siu Choi
*Assistant Examiner*—Bijan Ahvazi
(74) *Attorney, Agent, or Firm*—J. Peter Paredes; Rosenbaum & Silvert, P.C.

(57) ABSTRACT

A bioactive complex composition having enhanced oxidative stability, emulsion stability, mineral rich transparent beverages and a wide range of functional health benefits. The composition may include as a base composition individual ingredients or a synergistic blend of mineral salts, Omega-3 rich oils, phospholipids, chitosan, and alpha-casein, beta-casein, kappa-casein or protein fragments, glycopeptides, phosphopeptides. The composition may optionally be further utilized for the prevention of hypercholesterolemia, bone (and teeth) mineral loss, treatment of mental health diseases, heart health, additional nutritional supplementation, and treatment of additional medical conditions.

26 Claims, No Drawings

BIOACTIVE COMPLEXES COMPOSITIONS AND METHODS OF USE THEREOF

CROSS-REFERENCE TO RELATED APPLICATIONS

This application is a continuation in part of U.S. patent application Ser. No. 10/784,842 titled "Antioxidant Compositions and Methods of Use", recently filed on the 23 of Feb. 2004 which is hereby incorporated by reference with priority claims, and a continuation in part of U.S. patent application Ser. No. 11/306,582 titled "Nanoemulsion Compositions and Methods of Use", recently filed on the 3 of Jan. 2006 which is hereby incorporated by reference with priority claims.

FIELD OF THE INVENTION

The present invention relates to bioactive complex compositions, particularly compositions formed from natural ingredients, and methods for using said compositions to enhance efficacy and bioavailability of actives. The invention comprised of a polycationic complexation system further provides enhanced bioavailability of phospholipids, Omega-3 rich oils, oil soluble actives, and minerals for applications ranging from memory enhancers to oral care.

BACKGROUND

It is known that whatever their kind and origin, nutraceuticals and pharmaceuticals, that are not readily water soluble, have relatively limited bioavailability. Many factors are recognized in the art as limiting bioavailability including relatively limited membrane fluidity, solubility, unstable dispersions or emulsions. Additionally the presence of competing non-actives for the same enzymatic functionality, such as Omega-6 versus Omega-3. Mammals cannot interconvert the Omega-3 and Omega-6 fatty acids and their metabolism requires the same desaturation enzymes.

Numerous other competing interactions take place in vivo, including calcium and magnesium absorption, minerals required for enzymatic activation including zinc, acid intake and blood pH being too acidic, gastrointestinal and/or brain barrier permeation to name a few.

The presence of Omega-3 oils in food is of great importance since they cannot be synthesized by human and animal tissues and should thereby be provided with the diet. In tissues these essential fatty acids are converted to longer and more unsaturated fatty acids of the Omega-6 and Omega-3 families, such as arachidonic acid (AA), eicosapentaenoic (EPA), and docosahexaenoic (DHA), which are present in marine oils (fish, microalgae) in relatively high amounts. The health benefits of linoleic acid, alpha-linolenic acid, AA, EPA and DHA are well documented in the literature. These benefits include hypolipidemic, anti-thrombotic, and anti-inflammatory properties. They are also essential fats for growth, brain function, and visual acuity, especially for infants. Omega-3's are further recognized for their positive impact on psychiatric, brain, and neurologic conditions.

Many products ranging from functional foods and confectioneries to nutraceuticals and pharmaceuticals are emulsions or may be made into emulsions. An emulsion is a colloidal dispersion of two immiscible liquids, such as oil and water, in the form of droplets. If oil droplets are finely dispersed in water, then this is an oil-in-water or O/W emulsion. When water droplets are finely dispersed in oil, then this is a water-in-oil or W/O emulsion. O/W and W/O emulsions play a prominent role in the preparation of a wide range of products including foods, pharmaceutical products and cosmetics. It would be thus desirable to provide enhanced bioavailability compositions formed from natural ingredients and methods to effectively increase efficacy within highly polyunsaturated oils in O/W and W/O emulsions.

Numerous other products ranging from functional foods and beverages may incorporate powder actives. The powder's solubility and bioadhesion characteristics in vivo are of critical importance to the bioavailability of the functional active. It is also highly desirable for the powder to be delivered within a transparent beverage, or at other times having an opacifier impact. Regardless of the delivery system, it is always desirable for the delivery system to have a pleasing taste absent of bitterness. At other times, the powder's taste is desired to be salty, sweet, or even creamy thus adding taste functionality beyond the health and nutrition functionality.

Another significant area addressing the inclusion of functional actives centers around oxidation stability. One such prior art method is the utilization of a class of surface active agents or emulsifiers, as noted in the art U.S. Pat. No. 5,079,016 by Todd, Jr. on Jan. 7, 1992 titled "Color-stabilized carotenoid pigment compositions and foods colored therewith having increased resistance to oxidative color fading" includes surface active agents or emulsifiers with strong stabilizing and synergistic properties with natural antioxidants: sorbitan esters, such as mono and tri oleates and stearates, lactic acid esters of monoglycerides and diglycerides. Surface active agents or emulsifiers with strong stabilizing and modest synergistic properties include polyglycerol esters of fatty acids, such as octaglycerol monooleate, decaglycerol capric-caprylate, and decaglycerol tetraoleate, mono-diglycerides of fatty acids, such as glycerol mono oleate, acetylated monoglycerides, citric acid esters of mono-diglycerides, lecithin, and propylene glycol esters of fatty acids. The prior art notes an unexpected synergism exhibited between rosemary and sorbitan trioleate, as a preferred representative of the class of non-ionic surface active agents. This example shows that tocopherols significantly interact with these stabilizers to further improve the stability of the carotenoid pigments. This prior art identifies the importance of very specific and unique synergistic combinations.

SUMMARY OF THE INVENTION

The present invention relates to compositions and methods for enhancing the bioavailability and efficacy of a range of Omega-3 rich oils, minerals, and delivery systems thereof.

In addition, the compositions may offer nutritional and pharmacological benefits including: (1) enhanced membrane fluidity, having improved brain functions (e.g., memory, reduced ADD and ADHD, etc.) activity in animal bodies; (2) enhanced soluble complexes with calcium and chitosan for bioadhesion, providing remineralization of teeth and bone in animal bodies, (3) enhanced delivery of actives including the families of recognized fat-soluble antioxidants (tocopherols, tocotrienols, beta-carotene, coenzyme $Q_{10}$), choline, carnitine, and essential fatty acids (DHA, EPA).

Specific embodiments of the present invention are further described in the following detailed description.

DETAILED DESCRIPTION

The term "electron transfer", hereinafter also referred to as "ET", is the process by which an electron moves from one atom or molecule to another atom or molecule. ET is a mechanistic description of the thermodynamic concept of redox, wherein the formal oxidation states of both reaction partners change. Numerous essential processes in biology employ ET reactions, including: oxygen binding/transport, photosynthesis/respiration, metabolic syntheses, and detoxification of reactive species. Additionally, the process of energy transfer can be formalized as a two electron exchange (two concurrent ET events in opposite directions). ET reactions commonly involve transition metal complexes, but there are now many examples of ET in organic molecules. The term "electron transfer mediator", which is interchangeably used with electron transport mediator, is defined as means of increasing the effective mobilization of electrons including the tunneling or bridging across molecular scale interfaces. Without being bound by theory, an electron transfer mediator provides a low resistance path for electron mobility. The term "electron transfer bridge" is the coupling mechanism for intramolecular electron transfer between donor and acceptor.

The term "alkalide" is defined as a class of ionic compounds where the cations are of the Type I group (Alkali) elements Na, K, Rb, Cs (no known 'Lithide' exists). The cation is an alkali cation complexed by a large organic complexant. The resulting chemical form is A+ [Complexant]B−, where the complexant is a Cryptand, Crown Ether, or Aza-Crown.

The term "electride" is defined as being just like alkalides except that the anion is presumed to be simply an electron that is localized to a region of the crystal between the complexed cations.

The term "Omega-3" includes all enzymatically altered forms of Alpha-linolenic including Stearidonic acid, Eicosapentaenoic acid "EPA", and Docosahexaenoic acid "DHA".

The term "oil rich in Omega-3" includes all oils having greater than 20% Omega-3 content.

The term ubiquinone 50, 2,3-dimethoxy-5-methyl6-pentacontdacaenyl-benzoquinone is also hereinafter referred to as coenzyme $Q_{10}$ or CoQ10.

The present invention includes compositions and methods for enhancing bioavailability and efficacy of actives. The compositions have an impact in multiple categories including: antioxidation, mental health, immunity, bone health, triglyceride and total cholesterol reduction, and the modulation of metabolic pathways by influencing electron flux.

The compositions may enhance delivery of highly polyunsaturated lipids. They may include non-reducing sugars, sugar polyols, medium-chain triglycerides, sulfated polysaccharides, caseinophosphopeptides, phospholipids, chitosan and polyphenols. These compositions may be used in O/W or W/O emulsions or further subjected to post processing to yield free flowing powders as recognized in the art (e.g., spray drying, freeze drying, absorption plating, etc.).

Selected embodiments contain sulfated polysaccharides. These may include compounds containing at least one polymeric sugar moiety covalently attached to a sulfate group. One example of a sulfated polysaccharide is the carrageenan class of compounds. Other examples of sulfated polysaccharides include chondroitin sulfate, sulfated cyclodextrins, dextran sulfate and heparin sulfate.

The compositions may also include ingredients selected from the group of non-reducing sugars, sugar polyols, medium-chain triglycerides, polysaccharides, alpha-casein, beta-casein, kappa-casein or protein fragments, glycopeptides, phosphopeptides, alpha, beta, gamma or delta tocopherols, alpha, beta, gamma or delta tocotrienols, tocopherols, tocotrienols, beta-carotene, phospholipids and chitosan, or combinations thereof.

The compositions may also include pH modifiers including lactic acid, gallic acid, citric acid, ascorbic acid, gluconic acid, and chelating agents including citric acid, choline citrate or combinations thereof.

In selected embodiments, the compositions may include food, beverage, and confectionery ingredients including: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; cocoa powder; Sucralose; and combinations thereof.

The first embodiment of the composition is as a synergistic active as a means to provide superior protection of lipids (and other oxidative unstable products) against oxidation.

Antioxidation

A free radical is an active atom or molecule that has an unpaired electron in its outer shell. The free radical seeks to become stable by stealing an electron from another molecule. Unfortunately, while this results in the original molecule becoming stable, the second molecule becomes a free radical instead. The generation of free radicals can set off a chain reaction of free radical formation, as molecules seek to stabilize by grabbing electrons from the molecules surrounding them, and leaving new free radicals in their place. Antioxidants are molecules that can give up an electron to a free radical but do not become free radicals themselves.

The preferred embodiment is the presence of an electron transfer bridge, hereinafter referred to as ETB, across the interface of the O/W emulsion. The particularly preferred electron transfer bridge has an iron-sulfur cluster. The specifically preferred ETB is a chitosan-caprine CPP complex in which the enzymatically-modified caprine casein referred to as caseinophosphopeptide (CPP) is high in the sulfur-containing amino acid cysteine and the basic amino acid lysine (caprine CPP contains around 0.5% cysteine and 5% lysine whereas bovine CPP contains 0% cysteine and around 3% lysine). The iron content of the chitosan preparation should be between 50 and 400 ppm, particularly preferred at less than 200 ppm. The particularly preferred embodiment of the caprine CPP-chitosan complex is further comprised of a reducing sugar (e.g., glucose) within the oil phase, without being bound by theory attributed to thermal decomposition of reducing sugars and nitrogen-based compounds present in Omega-3 oil-based formulations previously stabilized with Vitamin E (mixed tocopherols or mixed tocotrienols). The thermal decomposition of reducing sugar (glucose)-amino acid (lysine)-glucosamine (chitosan) compounds are referred to as the Maillard browning reaction. The specifically preferred source of glucose molecules is a gamma-cyclodextrin-coenzyme Q10 inclusion complex from Wacker Chemical Corporation (Adrian, Mo., USA) under the commercial name of Cavamax CoQ10.sup.™ (75% glucose and 25% coenzyme Q10 on w/w %). It is the synergistic combination of glucose, cysteine, lysine, iron-containing chitosan and coenzyme Q10 that regenerates the tocopheryl free radicals into antioxidative tocopherol molecules). The Maillard browning reaction is initiated by condensation of a carbonyl group on the reducing sugar with free amino groups of amino acids, proteins, and peptides (caprine CPP), and amine groups of glucosamines (chitosan) thereby enhancing specific antioxidant activity in oil-in-water and water-in-oil emulsions.

The Cavamax CoQ10.sup.™ can be dissolved either in the oil or in the water phase. In the presence of strong chelating agents such as EDTA, lactoferrin and phytic acid, Cavamax CoQ10.sup.™ exhibits superior "protective" effect against oxidation of Omega-3 oils when added to the oil phase. Furthermore, the amount of Cavamax CoQ10.sup.™ can be reduced to levels below 0.5 wt. % when added directly to the oil phase. However, in the presence of weak chelating agents such as grape seed and grape pomace extract higher levels of Cavamax CoQ10.sup.™ are required. Cyclodextrins, which are ring shaped sugar compounds, are recognized in the art as a means to encapsulate Omega-3 oils to minimize oxidation of Omega-3 oil droplets by air, but the inclusion of cyclodextrins within the oil phase at a ratio of cyclodextrin to oil at less than 10 wt. % is unique (i.e., a ratio of cyclodextrin to oil of at least 10:1. The preferred level of cyclodextrin on a w/w % basis to the oil of less than 5 wt. %, particularly preferred is less than 1% on a w/w % basis to the oil. The specifically preferred cyclodextrin is a complex of gamma-cyclodextrin and coenzyme Q10. It is anticipated that fat soluble antioxidants, vitamins, or electron donor compounds complexed/encapsulated in gamma-cyclodextrin and then subsequently incorporated into the lipid/oil to provide superior protection against lipid oxidation. The preferred process method is to add Cavamax CoQ10.sup.™ to the oil phase followed by emulsification with egg yolk phospholipids to avoid encapsulating the caprine CPP-chitosan complex that contains added iron (chitosan lactate with added iron).

The key step of caprine CPP-chitosan complex preparation is adjusting the pH of the caprine CPP-chitosan complex solution to a range of pH 5.5-6.5, though the preferred embodiment has a pH 6.0 preferably with either potassium hydroxide or calcium hydroxide. Potassium hydroxide is the preferred pH adjuster except in situations resulting in too bitter taste in which calcium hydroxide achieves good results. Another alternative is the combination of both potassium hydroxide and calcium hydroxide with the ratio being determined by taste impact.

Lipid oxidation of O/W emulsions is promoted by endogenous transition metals that are naturally present in the oil, surfactant, and/or water. Iron is known to be more soluble at low pHs. Therefore, we anticipate lipid oxidation rates to be higher at pH 3.0 than 6.0. In the particular case of caprine CPP-chitosan complex, we are dealing with cationic oil-in-water emulsion droplets that oxidize more slowly than anionic emulsion droplets (at pH 3.0, chitosan exhibits a polycationic charge), without being bound by theory, because of their ability to repel cationic metals, thus decreasing interfacial iron concentrations and lipid oxidation rates. Water-soluble chelators inhibit lipid oxidation by binding aqueous-phase iron. Metal chelators however exhibit differences in iron binding potential. A recognized in the art superior metal chelator is EDTA. Iron bound to citrate can be more catalytically active than free iron. Therefore, citric acid is the least effective chelator at inhibiting lipid oxidation of the chelators tested (i.e., EDTA, malic acid, citric acid, fumaric acid, etc.) in the presence of iron. When citric and/or malic acid are used, the usage levels should be preferably less than 0.01% wt. (based on the weight of the emulsion) to chelate iron (or copper) and further preferably in applications stored at temperatures below 30° C. The specifically preferred organic acid is lactic acid (or it's derivative) due to the combined electron donor capacity and lack of catalytic impact.

Preferential Food & Beverage Specifications—Avoid

Avoid the fructose or fructose syrups in combination with Omega-3 oils and caprine CPP-chitosan complex. High fructose syrups, scientifically linked to the obesity pandemia, create thermal decomposition products of fructose-lysine (caprine CPP is 'rich' in the amino acid lysine), thus exhibiting more "pro-oxidant" and "genotoxic" activity as compared to the thermal decomposition products of glucose-lysine.

Avoid the combination of ascorbic acid (and ascorbyl palmitate) in the presence of iron, particularly at low pH conditions (pH<6.0) and especially when the phospholipids have iron within the oil/water interface such as egg yolk phospholipids. The result when used in combination with an Omega-3 rich oil is particularly pro-oxidant with ascorbic acid, which without being bound by theory the ascorbic acid keeps iron (III) in the reduced form of iron (II) that is highly prooxidant. Iron is less "prooxidant" at pH≧6.0.

Sodium chloride (NaCl) content should be as low as possible. Sodium chloride acts as pro-oxidant or antioxidant depending on the nature of the system involved.

Avoid using "plain" pectin, as the higher the content of methoxy groups present on the pectin molecule (less negative charges), the lower the interaction with the chitosan molecule (positively charged polymer at low pH).

Preferential Food & Beverage Specifications—Include

Antioxidants recognized in the art including vanillin, vanillin derivatives, bee propolis, grape seed extract, grape pomace extract, quercitin, tetrahydrocurcuminoids CG, ginger, turmeric, capsaicin, spirulina, Trolox (water soluble tocopherol by Hoffman Roche) and green tea (known to contain Superoxide Dismutase "SOD"), clove (according to USDA is nature's richest known source phytonutrient called eugenol, which enhances the metabolism of DHA, inactivates free radicals, and promotes nerve cell health), rosemary extract (especially high carnosic acid) and camosic acid derivatives, and walnut extracts. The addition of grape seed extract or grape pomace extract to O/W Menhaden oil-based emulsions treated with Cavamax CoQ10.sup.™ (0.91 wt. %) dispersed in the water phase (in the presence of the caprine CPP-chitosan complex of the present invention) exhibits high antioxidant activity after 21-days storage at 60° C. These grape-derived polyphenols exhibit both radical scavenging activity and mineral chelating activity.

Corn oil is the only plant oil high in ubiquinone (coenzyme Q) (200 ppm). Canola and soybean oil are high in gamma-tocopherol, recognized as having the highest antioxidant activity. Palm oil is high in mixed tocopherols and tocotrienols.

Ferulic acid is naturally present in extra-virgin olive oil, rice bran oil, corn, and oat oil. Curcumin is very similar to ferulic acid. The phytochemical ferulic acid is also found in the leaves and seeds of many plants, but especially in cereals such as brown rice, whole wheat and oats. Ferulic acid is also present in coffee, apple, artichoke, peanut, orange and pineapple. Ferulic acid is an antioxidant that neutralizes free radicals (superoxide, nitric oxide and hydroxyl radical) that could cause oxidative damage of cell membranes and DNA. Ferulic acid helps to prevent damage to our cells caused by ultraviolet light. Exposure to ultraviolet light actually increases the antioxidant potency of ferulic acid. Ferulic acid is often added as ingredient of anti-aging supplements. Studies have shown that ferulic acid can decrease blood glucose levels and can be of help to diabetes patients. Like many other antioxidants, ferulic acid reduces the level of cholesterol and triglyceride, thereby reducing the risk of hearth disease.

Fruit concentrate sweetener as humectant that comprises a blend of hydrolyzed starch having a dextrose equivalent (D.E.) of up to approximately 25; fruit juice or fruit syrup concentrate of at least approximately 40 wt. % soluble solids and approximately 0 wt. % insoluble solids thereby forming a liquor having a dry weight composition of approximately 40 to approximately 65 wt. % complex carbohydrates; and approximately 35 to approximately 55 wt. % simple sugars from the fruit juice or fruit syrup concentrate; and approximately 0 to approximately 5 wt. % nutritional components occurring naturally in the fruit juice or fruit syrup concentrate Galactolipids, such as from oat oil, also provide numerous benefits within the preferred embodiment. Galactolipids as recognized in the art protect O/W emulsions such that the lipids are not enzymatically degraded until the small intestine. The preferred embodiment is further comprised of galactolipids as a means to enable fat soluble nutraceutical and pharmaceutical actives incorporated into Omega-3 rich oils provide superior efficacy and bioavailability of both Omega-3 and their inclusive actives.

Gallic acid is preferably added to O/W marine oil-based emulsions at concentrations ≦50 ppm (0.005 wt. %, based on the weight of the emulsion). Gallic acid, found in plant materials such as blackberry bark, henna, tea, and as a component of hydrolyzable tannins, combats the browning effects that result from food processing. The antioxidant action of gallic acid and gallates is similar to that of other catechins, which behave as antioxidants by electron donation to free radical oxidants in aqueous solution.

Another implementation of the inventive technology is keratin (protein hydrolyzate/peptide obtained from wool (Cynatine FLX.sup.™, Keratec Corporation, New Zealand) complexed with the caprine CPP-chitosan of the present invention, or separately complexed with chitosan. Keratin can also be utilized as an alternative to caprine CPP, as keratin is also a sulfur-bearing protein.

Lactic acid is preferably included in the preparation of O/W emulsions, in particular at low pH, because lactic acid is an "electron donor" compound.

Utilize lactoferrin, preferably thermally-stabilized lactoferrin as comprised of proprietary ingredients of TAMUS 1408, and preferably further comprised of oils rich in ferulic acid. The inclusion of 1 mM lactoferrin or 5 mM phytic acid was included in an O/W emulsion comprised of Menhaden oil (OmegaPure.sup.™, Omega Protein Corporation, Houston, Tex., USA) blended with olive oil. Phytic acid is added at levels not higher than 0.05 wt. % (based on the weight of the emulsion) in the absence or presence of lactoferrin. It is important to isolate iron-containing proteins (e.g., lactoferrin) from the cyclodextrin, thus the inclusion of cyclodextrin is within the oil phase whereas lactoferrin is present in the water phase. As recognized in the art, the addition of bicarbonate improves the heat stability of iron-lactoferrin complexes thereby enhancing the oxidative stability of oil-in-water emulsions. Thus the infusion of carbon dioxide, at least during product storage, is anticipated to enhance shelf-life. The further inclusion of a cocktail of thermal stabilizing-compounds (i.e., TAMUS 1408) prevents the iron-lactoferrin complexes from undergoing denaturation (unfolding) during pasteurization at 90° C. for 3 minutes. Finally, chelating agents are known to stabilize lactoferrin, in particular EDTA (U.S. Pat. No. 7,034,126 and U.S. Pat. No. 7,026,295). Lactoferrin in combination with EDTA and caprine CPP-chitosan complex significantly inhibits lipid oxidation of O/W Menhaden-oil emulsions blended with Smart Balance Omega.sup.™ oil (U.S. Pat. No. 5,578,334). Transition metals decrease the oxidative stability of food emulsions through their ability to decompose lipid peroxides into free radicals. In food emulsions, free radicals are usually generated in the aqueous phase, and these radicals have important implications for the oxidation of emulsified oils.

Phospholipids "rich" in phosphatidylcholine (PC) such as those present in egg yolk phospholipids is the emulsifier of choice to increase "bilayer" adhesion between "negatively" charged phospholipids "rich" in PC and "positively" charged chitosan-CPP complex. Oil-in-water or water-in-oil emulsions containing oil droplets coated with phospholipids-caprine CPP-chitosan exhibit enhanced oxidative stability. Phosphatidyl serine (SerineAid 50P.sup.™) effectively inhibits iron-induced lipid peroxidation of egg yolk PC in emulsion droplets coated by anionic egg yolk PC and cationic caprine CPP-chitosan, indicating that incorporation of phosphoserine group into the phospholipid-cationic bilayers is helpful to enhance the oxidative stability of food lipids such as DHA and EPA. A water-soluble emulsifier GlycerolPhosphoCholine Hydrate 85% (GPC 85.sup.™) can also be added to the oil-in-water or water-in-oil emulsions to inhibit iron-induced peroxidation of egg yolk PC. The combination of SerineAid 50P.sup.™, GPC 85.sup.™ and egg yolk PC-caprine CPP-chitosan results in synergistic inhibition of lipid oxidation, because multicomponent antioxidant systems can inhibit oxidation at many different phases of oxidation. SerineAid.sup.™ and GPC 85.sup.™ decrease the number of free radicals generated in a system by inhibiting metal-catalyzed oxidation.

The further inclusion of phytic acid enhances the oxidative stability. Phytic acid is a powerful inhibitor of iron-driven radical (•OH) formation because of its ability to form a unique iron chelate that becomes catalytically inactive. Unlike most other iron chelates, $Fe^{3+}$-phytate does not retain a reactive coordination site, thus it does not support •OH generation.

The polyphenols found in tea are more commonly known as flavanols or catechins and comprise 30-40 percent of the extractable solids of dried green tea leaves. The main catechins in green tea extract are epicatechin, epicatechin-3-gallate, epigallocatechin, and epigallocatechin-3-gallate (EGCG), with the latter being the highest in concentration. Green tea leave oils have demonstrated significant antioxidant, anticarcinogenic, anti-inflammatory, thermogenic, probiotic, and anti-microbial properties in numerous human, animal, and in-vitro studies. Green tea extracts are a natural source of gallic acid, which is a preferred antioxidant playing a particularly synergistic role with Cavamax CoQ10.sup.™. Coenzyme Q10 with d-limonene contains smaller, nano-sized coenzyme Q10 particles that enhance this absorption into other oils/fats. Cavamax CoQ10.sup.™ dissolved at 0.91 wt. % in the "water" phase of the O/W Menhaden oil-based emulsion "regenerates" the tocopheryl radicals (prooxidant activity) into antioxidative tocopherol molecules (antioxidant activity) when the caprine CPP-chitosan complex is used with polyphenols, in particular with grape seed extract. Electron transfer mediators (i.e., potassium hydroxide, calcium hydroxide, magnesium hydroxide) are essential to "activate" the aromatic rings, such as those present in the polyphenol(s) and coenzyme Q10 molecules. The gas chromatography (GC) data of O/W Menhaden oil-based emulsions treated with caprine CPP-chitosan complex, polyphenols (grape seed extract, grape pomace extract, bee propolis), Cavamax CoQ10.sup.™ (dissolved in the water phase at a level of 0.91 wt. % based on the weight of emulsion), and the preferred electron transfer mediator potassium hydroxide (used to adjust the pH of the O/W Menhaden-oil based emulsions to 6.0) after 28 days storage at 60° C. are as follows: Control (formulation only): 100% (decomposition into hydroperoxides), Grape seed extract: 4.09%; Grape Pomace Extract: 23.19%; and Bee Propolis: 33.92%. The number of GC peaks (oxidation volatile products) present in the treated samples is decreased (4 or 3 peaks) as compared to the control sample that has a total of 20 peaks. Each individual peak is associated with an aldehyde compound (decomposition product of hydroperoxides). One preferred embodiment is the polyphenols derived from the fruit of *Solanum melongena*.

Potassium salt, preferably monobasic potassium phosphate, is the preferred buffering agent because potassium phosphate is used in the food and pharmaceutical industries to "sequester" deleterious trace minerals (iron, copper), to provide potassium ions to the formulation, and to play an active role in the electron transport process. The major mineral "activator" in vivo within cells is potassium, which is present in healthy cells at levels 20 times those of sodium. In other words, potassium is an "activator of metabolic functions" in vivo, in addition to the "in-food" role of electron transport. Thus, the potassium salt serves a multifunctional role of buffering agent, chelating agent, electrolyte, and electron transport mediator.

Sodium oleate is recognized in the art as a means to reduce micelle size within emulsions.

Sterols in oat oil are recognized in the art as a mean to protect oils against deterioration at frying temperatures.

Transglutaminase (TG) is known to interact with alpha-.sub.s1-casein and form the basis of milk-protein-based edible films and coatings.

Utilize trehalose, a naturally occurring osmolyte, to stabilize the caprine CPP-chitosan complex and help retain the activity of caprine CPP (and lactoferrin) in solution as well as in the freeze-dried state. The preferential hydration of the caprine CPP-chitosan complex by trehalose, without being bound by theory, enables the electron tunneling or mean free path to be increased as a means to enhance electron transfer into the water phase.

The inventive composition further includes methods to stabilize lipids that are not prepared as emulsions.

Stabilized Oil (as Compared to Emulsion)

It is recognized that electron transfer within the non-conductive oil phase is poor. This in combination with the oil being susceptible to oxidation through the presence of dissolved oxygen, pro-catalysts such as iron, and peroxides, the generation of free radicals (even in the presence of antioxidants) creates oxidation by-products. The failure to create a high-surface area "pathway" for the electrons to transfer or tunnel limits the range of the free radical electron distance to the mean free path. In the event that the antioxidant is not present within this range, the free radical creates oxidative by-products. Without being bound by theory, the presence of components within the oil phase that provide the free radical with a low electrical resistance pathway to the antioxidant will enable the free radical to seek an electron from the antioxidant rather than damaging the lipid molecules within the oil phase.

The preferred embodiment is a protein-chitosan or peptide-chitosan complex whereby the chitosan provides binding capacity with the host oil. The particularly preferred protein or peptide is a sulfur bearing-protein. The particularly preferred chitosan has iron present, such that the caseinophosphopeptide-chitosan complex creates an iron-sulfur cluster. The protein or peptide is preferably further comprised of divalent mineral salts such as inorganic calcium, magnesium, and zinc salts (i.e., calcium chloride, magnesium chloride, zinc chloride) or organic calcium, magnesium, and zinc salts (i.e., calcium lactate, magnesium lactate, zinc lactate). Milk mineral (TruCal.sup.™, Glanbia Foods, Twin Falls, Id., USA) exhibits a synergistic antioxidant effect with the caprine CPP-chitosan complex in O/W Menhaden oil-based emulsions. The specifically preferred caprine CPP-chitosan complex is further complexed with at least one selected from the group consisting of trehalose, ribose, glucose, or cyclodextrins. The preferred gamma-cyclodextrin encapsulates at least one selected from the group consisting of coenzyme Q10, mixed tocopherols, mixed tocotrienols, or additional oil soluble antioxidants.

The preferred manufacturing process incorporates polyols, or preferably trehalose or ribose prior to drying by means known in the art including spray drying and freeze drying.

The preferred oil is further comprised of at least one selected from the group consisting of ionic liquids, ionic emulsifiers, absorbed carbon dioxide, polyphenols, gallic acid, green tea extracts, chelators including EDTA, synthetic antioxidants including BHA, BHT, and TBHQ.

Other Functional Roles

The oxidative stability testing with lactoferrin was conducted under experimental conditions (i.e., pH, ionic strength) that favor "electrostatic" and "hydrophobic" interactions. Electrostatic and hydrophobic interactions are crucial for the biological activity of lactoferrin (i.e., antimicrobial activity, anticancer activity). Protein-lipid interactions, possible electrostatic, involving lipid-binding-induced structural changes to lactoferrin, are inferred by sodium dodecyl sulfate polyacrylamide gel electrophoresis (SDS-PAGE) and analytical ultracentrifugation (AU). The incorporation of oils having Omega-3, Omega-6, and Omega 9 induces structural changes to lactoferrin through lipid-binding, which have a significant role on the biological activity of lactoferrin. The preferred oil has the presence of ferulic acid, with the particularly preferred oil being selected from the group consisting of rice bran oil or virgin olive oil. The specifically preferred oil is the Smart Balance Omega.sup.™ oil, which is a commercial oil blend containing canola, soybean and olive oils (Heart Beat Foods, Cresskill, N.J., USA) designed to increase the HDL concentration and the HDL/LDL ratio (U.S. Pat. No. 5,578,334).

A preferred embodiment as a means to reduce triglycerides and total cholesterol is the combination of vanillin (or o-vanillin, fat-soluble vanillyl acylamides) and gallic acid and at least one selected from the group consisting of EDTA, coenzyme Q10 encapsulated by gamma-cyclodextrin, thermally-stabilized lactoferrin (or EDTA), mixed tocopherols, mixed tocotrienols, or combinations thereof. A particularly preferred embodiment is the combination of vanillin, gallic acid or green tea extracts, EDTA or thermally-stabilized lactoferrin, mixed tocopherols and tocotrienols, and coenzyme Q10 encapsulated by gamma-cyclodextrin all within an oil rich in Omega-3 further encapsulated by an oil rich in ferulic acid. Vanillin reacts preferentially with protein lysine residues. Thus the specifically preferred embodiment is further comprised of caprine CPP-chitosan complex. The prior art of U.S. Pat. No. 6,599,522 by Mokshagundam et. al., on Jul. 29, 2003 titled "Triglyceride reducing agent" utilizes ascorbic acid and EDTA. Ascorbic acid functionality is limited by the pH sensitivity of the host environment, whereas gallic acid is not and further gallic acid in combination with Cavamax CoQ10.sup.™ is critical to the regeneration of tocopheryl free radicals (prooxidant activity) into antioxidative tocopherol molecules (antioxidant activity) within an Omega-3 rich oil. EDTA is a synthetic chelator/antioxidant having known toxicity, whereas lactoferrin is a natural bioactive milk protein exhibiting both iron-chelating activity and numerous recognized benefits including enhanced immunity.

The preparation of the caprine CPP-chitosan complex is one of the most critical steps in achieving the many functional benefits. One exemplary method to prepare the CPP is as follows.

CPP Preparation

Four versions of HEC chitosan (M-40L, M80L, FM-40L, FM-80) were prepared in which iron ($\leq 200$ ppm), lactic acid, and sufficient calcium, potassium, or magnesium hydroxide to adjust pH to 6.0 were added followed by freeze-drying. The freeze-dried chitosan preparations were subsequently used to prepare the caprine CPP-chitosan complex (Meyenber's goat milk) again followed by freeze-drying. The HEC chitosans (M-40L, M80L, FM-40L, and FM-80) complexed with caprine CPP exhibit 'good' antioxidant activity in O/W Menhaden oil-based emulsions stored at 40° C. for 7 days. Since the HEC chitosans are "free" of protein, the thermal decomposition of reducing sugar-amino-amine compounds (Maillard reaction products) are expected to be smaller than those of Orcas' and Cargill's chitosans. This means 'lower' antioxidant activity of HEC chitosans than those of Orcas' and Cargill's chitosans. In the case of chitosan lactate manufactured by Pronova Biopolymers Corporation, the formation of caprine CPP-chitosan complex was achieved by adjusting the pH to 6.0 with around 5 ml of 0.1 N potassium hydroxide. In the case of Orcas' chitosan or Cargill's chitosan around 50 ml of 0.1 N potassium hydroxide was added resulting in chitosan-CPP preparation excessively bitter and hygroscopic. Therefore, the preparation of Orcas' chitosan or Cargill's chitosan must use calcium hydroxide, magnesium hydroxide, or mineral milk TruCal.sup.™ (Glanbia Foods, Twin Falls, Id., USA) to avoid these detrimental effects on flavor and storage stability of caprine CPP-chitosan preparations.

Additional testing has been performed using a variety of chitosan forms, resulting in the preferred chitosan that have trace amounts of iron. Alternatively, a pure form of chitosan can be complexed with iron with the resulting chitosan-iron complex being used to achieve comparable iron levels as present in the Pronova's chitosan (i.e., less than 200 ppm). The more preferred chitosan is a non-shellfish source chitosan such as resulting from fermentation process of the fungi *Aspergillus niger* as available from Cargill Food & Pharma Specialties (Cedar Rapids, Iowa, USA). The specifically preferred chitosan salt is chitosan lactate. Chitosan as chitosan-alpha lipoic acid complex is also a particularly potent component of the antioxidant and/or nanoemulsion compositions. Thiolated chitosan is additionally a multifunctional chitosan form that has the secondary benefit of being a superior bioadhesive and mucoadhesive. The superior calcium absorption, without being bound by theory, may be attributed to the increased mucoadhesive properties within the gastrointestinal tract yielding controlled release of the caprine CPP. A thiolated chitosan includes chitosan-4-thio-butyl-amidine (a.k.a. chitosan-TBA). The further addition of glutathione, most notably reduced glutathione, yields superior bioadhesive properties.

It is important to note that chitosan that is void of iron also serves a critical role, which is enhancing the emulsion stability. Iron, which is a known catalyst for oxidation, cannot be in an excessive amount without moving into a prooxidant scenario.

The preparation of the emulsion is also another critical step, with the following method being an exemplary method.

Emulsion Preparation

The resulting caprine CPP-chitosan complexes were each added to O/W Menhaden oil-based emulsions blended with Smart Balance Omega.sup.™ oil (12.5% Menhaden and 12.5% Smart Balance Omega.sup.™ oil) in the absence and presence of caprine CPP-chitosan complex at pH 6.0. All samples were further comprised of Cavamax CoQ10.sup.™ and egg yolk phospholipids (Omega 6-PL-85.sup.™). After 7 days storage at 40° C. the p-anisidine value for each treatment is as follows: Treatment 1 (control) (4.25); treatment 2 (M-40L and CPP) (3.60); treatment 3 (M80L and CPP) (3.54); treatment 4 (FM-40 and CPP) (3.61); and treatment 5 (FM-80 and CPP) (3.59). Food-Grade EDTA (30 ppm w/w, based on the weight of the oil) was used as a chelating agent in treatments T2 thru T5.

In other embodiments, the compositions may be made into products including: hypercholesterolemia prevention products in a mammal comprised of calcium and magnesium salts; bone mineral loss prevention products in a mammal comprised of calcium and magnesium salts; oils rich in Omega-3 products comprised of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; microalgae oils rich in Omega-3, or conjugated linoleic acid, or combinations thereof; beverage products being transparent comprised of calcium and magnesium salts; cocoa products having improved creaminess, reduced bitterness, and reduced oxidation; protein rich products, comprised of high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

The present invention may function as an antioxidant in a variety of ways. For instance, sucrose has demonstrated its potential as a fat-solubilizing agent for natural vitamins such as provitamin A (beta-carotene) and vitamin E (tocopherol) as well as polyphenolic compounds and caprine CPP and as an antioxidant agent (invert sugar) in fat emulsions.

The compositions may also include polysaccharides such as sulfated polysaccharides. Sulfated polysaccharides may include iota-, kappa-, or lambda-carrageenan, or combinations thereof.

Compositions of the present invention may also include alpha-casein, beta-casein, kappa-casein or protein fragments, glycopeptides, phosphopeptides and combinations thereof. Phosphopeptides may include phosphopeptides high in alpha.sub.s2.-casein and medium-chain triglycerides such as caseinophosphopeptides (CPP). CPP may be isolated from caprine (goat) milk. CPP have a particularly potent ability to form soluble complexes with calcium. The increased solubility of the calcium-bound caprine CPP-chitosan complex may further enhance the mineral absorption to remineralize teeth, especially through the chitosan adhesion within the oral cavity.

Compositions may further include alpha, beta, gamma or delta tocopherols, alpha, beta, gamma or delta tocotrienols, tocopherols, tocotrienols, beta-carotene, phospholipids, chitosan or combinations thereof. A preferred mix of tocotrienols and tocopherols is extracted from palm sources.

The compositions may also include polyphenols. A preferred polyphenol is derived from the fruit of *Solanum melongena*. Additional preferred polyphenols are derived from apple, cocoa, grapes, pomegranate, and tea.

Fat emulsion particles containing sucrose or sorbitol increase the solubility (and therefore, dispersion) of tocopherol (vitamin E) and beta-carotene (provitamin A) present in flaxseed oil. Fat particles containing sucrose or sorbitol will also increase the solubility (dispersion) of cocoa (polyphenolic compounds), eggplant-carrageenan complex (polyphenolic compounds) and caprine caseinophosphopeptide-chitosan complex. The enhanced antioxidant activity observed in O/W emulsions containing Canadian flaxseed oil stems from the cooperation among tocopherols, beta-carotene, phospholipids, sorbitol, proprietary cocoa mix, and selected antioxidant compositions of the present invention. The chitosan further enhances bioadhesion, which for oral consumption of actives further improves the efficacy of the active by encouraging sublingual and buccal administration thus avoiding gastrointestinal deterioration.

Phospholipids used in embodiments of the invention may include phospholipids from the group of egg yolk, soybean phospholipids, or combinations thereof. TBA studies confirm the synergistic antioxidant effects among soybean phospholipids (lecithin), beta-carotene (provitamin A), tocopherol (vitamin E), and sorbitol (sugar alcohol) or sucrose (non-reducing sugar) in flaxseed oil-based nanoemulsions. The resulting flaxseed oil-based nanoemulsions and the further use of soybean phospholipids, sorbitol or sucrose along with homogenization minimize the lipid oxidation of Omega-3, Omega-6, and Omega-9 fatty acids. The shelf life of these essential polyunsaturated fatty acids (Omega-3, Omega-6, Omega-9) in O/W nanoemulsions are therefore greatly extended by some antioxidant compositions of the present invention. Identical benefits are realized with a proprietary cocoa mix and subsequent high-pressure homogenization.

Lecithin is widely used in lipid-based food products as an antioxidant synergist. The structure of phospholipid molecules enables lecithin to establish a protective coating on the surface of the oil droplet, thereby retarding lipid oxidation. The process of homogenization entraps not only the phospholipid molecules but also the tocopherol and beta-carotene molecules in the oil droplets that result in enhanced protection against lipid oxidation. The production of low-fat products is further improved by the method of incorporating selected antioxidant compositions of the invention and egg yolk phospholipids to impart a rich and creamy mouthfeel characteristic in low-fat products. Lecithin also has importance in increasing efficacy due to the choline present.

Phosphatidylcholine is a phospholipid that is a major constituent of cell membranes. Choline comprises about 15 wt. % of the weight of phosphatidylcholine. Phosphatidylcholine is also known as PtdCho or lecithin. Lecithins containing phosphatidylcholine (PC) are produced from vegetable, animal and microbial sources, but mainly from vegetable sources. Soybean, sunflower and rapeseed are the major plant sources of commercial lecithin. Soybean is the most common source. Eggs themselves naturally contain from 68 to 72 wt. % phosphatidylcholine, while soya contains from 20 to 22 wt. % phosphatidylcholine. Phosphatidylcholine is important for normal cellular membrane composition and repair. Phosphatidylcholine is also the major delivery form of the essential nutrient choline.

Choline itself is a precursor in the synthesis of the neurotransmitter acetylcholine, the methyl donor betaine and phospholipids, including phosphatidylcholine and sphingomyelin among others. Phosphatidylcholine's role in the maintenance of cell-membrane integrity is vital to all of the basic biological processes. These are: information flow that occurs within cells from DNA to RNA to proteins; the formation of cellular energy and intracellular communication or signal transduction. Choline is an essential component of phospholipids, and is the building block for acetylcholine, a major neurotransmitter of the central nervous system. When a declining choline level becomes a limiting factor in the synthesis of acetylcholine, which can occur during exercise and other stressful activities, peak physical and mental performance can be affected. Choline has also been shown to potentiate the secretion of human growth hormone (hGH), a master hormone that in part regulates basal metabolism and hence body composition. Since the intrinsic release of hGH declines significantly after adolescence, manifestations are seen as diminished resistance to illness, vitality, and recovery, losses in muscle mass, increases in fat mass, and negative changes in sleep patterns.

Phosphatidylcholine, particularly phosphatidylcholine rich in polyunsaturated fatty acids, has a marked fluidizing effect on cellular membranes. Decreased cell-membrane fluidization and breakdown of cell-membrane integrity, as well as impairment of cell-membrane repair mechanisms, are associated with a number of disorders, including liver disease, neurological diseases, various cancers and cell death. A particular preferred phospholipid rich in phosphatidyl choline is derived from egg yolks (Omega-6-PL-85.sup.™) manufactured by Belovo Incorporated (Pinehurst, N.C., USA).

The further inclusion of additional sources of choline and phosphatidyl containing compounds is anticipated as yielding enhanced efficacy and benefits themselves as recognized in the art for a wide range of psychiatric, brain, and other functional benefits. Exemplary compounds include phospatidylserine, alpha-glyceryl phosphoryl choline, and choline citrate. Scientific research and clinical investigations have shown that phosphatidylserine, for example, plays a critical role in maintaining optimal mental performance. A particular preferred phospholipid rich in phosphatidylserine is SerineAid 50 P.sup.™ (Chemi Nutraceuticals, White Bear Lake, Minn., USA). Another particularly preferred phospholipid is alpha-glyceryl phosphoryl choline (GPC 85.sup.™) from Science & Ingredients Corporation (Carlshad, Calif., USA). (GPC 85.sup.™) is comprised of 15 wt. % water and 85 wt. % GPC).

The further addition of pH modifiers including lactic acid, gallic acid, sodium acid sulfate, citric acid, ascorbic acid, gluconic acid or combinations thereof may improve the oxidative stability. The yet further addition of chelating agents including citric acid may also enhance the oxidative stability. Although citric acid controls the conversion of sucrose to invert sugar, accelerated storage conditions (i.e., a temperature of 60° C. for more than 7 days) can lead to the formation of invert sugar (a mixture of glucose and fructose). Enhanced solubility may reduce the chalkiness associated with precipitated compounds, an important criteria in the inclusion of the nanoemulsions in functional foods, confectioneries, and beverages for superior texture and mouthfeel.

In a specific embodiment, the invention includes a composition having ingredients selected from the group of: non-reducing sugars, sugar polyols, or combinations thereof; modified starches; polysaccharides; glycerides selected from enzymatically modified oils, fats, and fatty acids of mono-, di-, and tri-glycerides; glycerides selected from lipolyzed modified oils, fats, and fatty acids of mono-, di-, and tri-glycerides; fruit concentrate sweetener as humectant that comprises a blend of hydrolyzed starch having a dextrose equivalent (D.E.) of up to approximately 25; fruit juice or fruit syrup concentrate of at least approximately 40 wt. % soluble solids and approximately 0 wt. % insoluble solids thereby forming a liquor having a dry weight composition of approximately 40 to approximately 65 wt. % complex carbohydrates; and approximately 35 to approximately 55 wt. % simple sugars from the fruit juice or fruit syrup concentrate; and approximately 0 to approximately 5 wt. % nutritional components occurring naturally in the fruit juice or fruit syrup concentrate; cocoa powder; Sucralose; or combinations thereof.

Cocoa powder contains around 20 wt. % raw protein. Maillard reactions are initiated by a condensation between the free amino group of amino acid, peptide, or protein and the carbonyl group of a reducing sugar to give a N-substituted glycosyl-amino compound followed by the reversible formation of the Schiff base, which cyclizes to the NB substituted glycosylamine and its then converted into the Amadori compound. The Amadori rearrangement is catalyzed by weak acids and is considered the key step of the Maillard reaction. Amadori compounds formed during the early stage of the Maillard reaction are responsible for the loss of nutritional value of amino acids and proteins, because their biological activity is reduced by the formation of Amadori compounds. Cocoa powder also contains around 10 wt. % polyphenols, which have antioxidative effects (Dreosti I. E. in Nutrition 16, 692-694 (2000)). The ability of cocoa powder to inhibit lipid oxidation in O/W emulsion systems with added sucrose (pH 6.6) is influenced by heat treatments. An extensive acid hydrolysis of sucrose, by heat, is detrimental to the antioxidant capacity of cocoa powder. However, for formulated O/W emulsions that have sorbitol (pH 6.6), cocoa powder shows enhanced oxidative stability upon storage at 60° C. for 28 days.

A wide range of products may be manufactured by inclusion of the compositions of the invention including: hypercholesterolemia prevention products in a mammal including salts selected from the group of calcium and magnesium salts; bone mineral loss prevention products in a mammal including salts selected from the group of calcium and magnesium salts; oils rich in Omega-3 products, further comprised of salts selected from the group of calcium and magnesium salts; oil-soluble flavor products; oil-soluble vitamin, nutraceutical, or pharmaceutical products; products having vegetable oils including rice bran oil, flax, chia, hemp, castor, soybean, lesquerella, dehydrated castor oil, rich in Omega-3, or conjugated linoleic acid, animal oils including fish, egg, poultry, and beef oils rich in Omega-3, or conjugated linoleic acid, or combinations thereof; microalgae oils, rich in Omega-3, or conjugated linoleic acid, or combinations thereof; beverage products being transparent including salts selected from the group of calcium and magnesium salts; cocoa products having improved creaminess, reduced bitterness, and reduced oxidation; protein rich products including high-methoxyl pectins or pectin alginates or combinations thereof having reduced protein settling and sedimentation; protein rich products having reduced protein settling and sedimentation; oil-in-water micro- and nano-emulsions having increased emulsion and oxidation stability; or water-in-oil micro- and nano-emulsions having increased emulsion and oxidation stability.

Additional preferred actives include actives that further enhance transport through cellular membranes/mitochondria. One exemplary is Acetyl L-carnitine, an amino acid-like compound related to choline. It is a brain support supplement that may assist in the conversion of choline into acetylcholine, one of the body's key neurotransmitters. Additional L-carnitine components include components selected from the group consisting of free L-carnitine, L-carnitine L-tartrate, L-carnitine magnesium citrate and acetyl-L-carnitine.

The acetyl group that is part of acetyl-L-carnitine contributes to the production of the neurotransmitter acetylcholine, which is required for mental function. Several double-blind clinical trials suggest that acetyl-L-carnitine delays the progression of Alzheimer's disease and enhances overall performance in some people with Alzheimer's disease. Alzheimer's research has been done with the acetyl-L-carnitine form, rather than the L-carnitine form, of this nutrient. L-carnitine is traditionally made in the body from the amino acids lysine and methionine, and is needed to release energy from fat. It transports fatty acids into mitochondria, though the body requires adequate lysine, methionine, vitamin C, iron, niacin, and vitamin B6 to produce carnitine.

Additional preferred actives include actives that suppress delta-5 desaturase enzyme. A more preferred active is sesame lignans, an extract from sesame seeds. A series of specific actives are found in sesame lignans including sesamin and sesamol. Sesame lignans suppress the enzyme (delta-5 desaturase) that converts DGLA into arachidonic acid. By blocking the undesirable enzyme (delta-5 desaturase), more DGLA is available for conversion into beneficial prostaglandin.

Yet further additional actives include permeation enhancers, with exemplaries including acylcarnitine, phosphatidylcholine, fatty acids (eicosapentaenoic acid (EPA), docosahexaenoic acid (DHA), oleic acid, capric acid, linoleic acid, and their monoglycerides), bile salts (cholate, taurocholate and derivatives), salicylates (3- or 5-methoxy-salycilate, salicylate), homovanilate, surfactants (sodium dodecyl sulfate (SDS), Triton X-100, Brij), chelating agents (ethylenediamine tetraacetic acid (EDTA), citric acid, phytic acid, enamine derivatives), and aprotinin.

The inclusion of such permeation enhancers, in combination with the small size of the nanoemulsion composition enables permeation through various administration routes including the skin, blood capillary or membrane barriers. Therefore, the nanoemulsion composition is suitable for dermal, peroral, enteral, parenteral, ocular, pulmonary, and transmucosal administration routes. The term "permeation enhancer" includes all actives and methods that promote permeation through the cellular membranes, such as mitochondria of cells including, though not limited to, gastrointestinal, and brain cells.

Additional functionality includes enhancing cognitive performance, and reducing disorders of mental health. The use of specific actives such as cholines and serines is recognized in the art for the treatment of a wide range of cognitive and mental health disorders. These include as one exemplary, though not limited, enhancing memory functions in Alzheimer patients. The present invention uniquely achieves a synergistic impact on such cognitive and mental health conditions by enhancing the delivery of such actives and concurrently the delivery of Omega-3. The realized benefits are greater than each individual component.

The range of products include, but are not limited to, confectionery, baked goods, spreads, dressings, salad dressings, nutraceutical supplements, functional foods products, ice cream, seed milks, dairy products, pharmaceutical tablets, syrups, and medicines, functional confectionery products, mineral-enriched drinks, and oral care products. The specific complexation of caseinophosphopeptide (CPP) with chitosan further leverages the bioadhesive properties of chitosan, thus the complex may provide both superior solubility for the calcium and adhesion to the teeth both of which are required conditions for teeth remineralization.

Compositions of the present invention may include O/W and W/O emulsions prepared with vegetable and animal oils that contain a significant amount of highly polyunsaturated fatty acids such as rice bran oil, flaxseed oil, chia oil, hemp oil, soybean oil, lesquerella oil, castor oil, dehydrated castor oil, menhaden oil, sardine oil, herring oil, salmon oil, anchovy oil, and other oils rich in Omega-3, or conjugated linoleic acid. The oil content of the O/W and W/O emulsions may vary according to the oil species component used and other components but may be within the range of 0.1-95 w/v %, preferably 1-85 w/v %. Embodiments of the present invention also may be effective when applied to oil flavors such as fruit and herb flavored oils, cheese flavored oils, butter flavored oils, and oil soluble vitamin, nutraceutical or pharmaceutical products.

Oil-in-water (O/W) emulsions that include small lipid droplets dispersed in an aqueous medium form the basis of many kinds of foods, e.g., milk, cream, beverages, dressings, dips, sauces, batters and deserts. Emulsions are thermodynamically unstable systems because of the unfavorable contact between oil and water phases, and because the oil and water phases have different densities, hence they will always breakdown over time. Use of emulsifiers, which are surface-active ingredients that absorb to the surface of freshly formed lipid droplets during homogenization, usually retards emulsion breakdown. Once absorbed, they facilitate further droplet disruption by lowering the interfacial tension, thereby reducing the size of the droplets produced during homogenization. Emulsifiers also reduce the tendency for droplets to aggregate by forming protective membranes and/or generating repulsive forces between the droplets. A good emulsifier should rapidly adsorb to the surface of the lipid droplets formed during homogenization, rapidly lower the interfacial tension by a significant amount and protect the droplets against aggregation during emulsion processing, storage and utilization.

Emulsions prepared with egg yolk phospholipids and the nanoemulsion compositions of the present invention have improved stability against phase separation and particle aggregation. Recent studies for the purpose of enhancing flavor release have shown that the release of non-polar flavors from O/W emulsions during mastication is controlled by encapsulating the oil droplets within biopolymer particles (Malone et al. in Flavor Release, ACS Symposium Series, American Chemical Society, pp. 212-217 (2000)). Biopolymer particles are created by the caprine caseinophosphopeptide-chitosan complex and eggplant-carrageenan complex that are embodiments of the inventive antioxidant compositions.

Different emulsifiers are categorized as being ionic or non-ionic. Ionic compounds may be cationic, anionic or amphoteric. Ionic emulsifiers have a problem; however, they can react with various ions to form complexes that adversely affect performance. Non-ionic emulsifiers tend not to react with ions and are used most extensively in the food industry. Without being bound by theory, the presence of a non-ionic surface active agent limits the creation of adverse complexes with the polycationic CPP-chitosan complex. The utilization of non-ionic components is desired within the oil and water interface. Whereas, the preferred oil soluble components within the oil phase are ionic as a means to increase the electrical conductivity and/or electron transport such that electron transport can be enhanced from antioxidant and/or electron donor within the oil phase and/or through the interface (preferably through CPP-chitosan emulating channel proteins) such that water soluble antioxidants become the preferred electron donor (as the water phase has higher electrical conductivity and/or electron transport). The particularly preferred embodiment is where the "channel protein" is a phosphopeptide. Without being bound by theory, the negative charge of the phosphate group enhances the electron transfer across the liquid-liquid interface. It is recognized in the art that prior binding of ubiquinone (i.e., CoQ10) to protein followed by the subsequent binding of phospholipids is a means to reactive enzymatic reactions. The preferred embodiment is further comprised of whey protein—lactic acid—CoQ10 complex to further encapsulate the Omega-3 rich oil emulsion.

One exemplary non-ionic surface active agent is polyglycerol. One method known in the art to solubilize organic carboxylic acids is through the utilization of diglycerides. The inventive preferred embodiment is comprised of carboxylic acids selected from the group consisting of lactic acid, gallic acid, or combinations thereof. The particularly preferred is the combination of lactic acid and gallic acid, without being bound by theory, is attributed to lactic acid's and gallic acid's superior electron donor capacity.

One exemplary ionic emulsifier, which is preferentially oil soluble, is lecithin (or phosphatidyl choline). Lecithin is unique in that it is both able to be dissolved in oil and carry a charge (critical for electron transport). The conductivity of the host oil can be modified using ionic emulsifiers, as noted in the art, such as lecithin and charged compounds with a hydrophobic end such as alcohols. The preferred embodiment only utilizes charged compounds with a hydrophobic end, such as alcohol, which is limited to solutions absent of proteins such as the particularly preferred embodiment, as it cause protein precipitation (i.e., CPP-chitosan).

The caseinophosphopeptide (CPP) employed as nanoemulsion compositions of the present invention may include alpha.sub.s2-casein as isolated from caprine (goat) milk. Caseins and caseinophosphopeptides exhibit different degrees of phosphorylation, and a direct relationship between the degree of phosphorylation and mineral chelating activity has been described (Kitts, D. D. in Can. J. Physiol. Pharmacol. 72, 423-434 (1994)). Accordingly based on phosphorylation, alpha.sub.s2-casein>alpha.sub.s1-casein>beta-casein>kappa-casein. Caseinophosphopeptide isolated from caprine (goat) milk high in alpha.sub.s2-casein (alpha.sub.s2-casein=29.2% of total casein) has more mineral chelating activity than a caseinophosphopeptide isolated from bovine (cow) milk (alpha.sub.s2-casein=12.1% of total casein). The phosphoric group of phosphoserine and carboxic groups of acidic amino acids present in the caseinophosphopeptide isolated from caprine (goat) milk high in alpha.sub.s2-casein, without being bound by theory, likely complexes with metal ions such as iron and copper. Complexation with other critical nutritional minerals, such as selenium, zinc, and magnesium may further increase their bioavailability.

It would also be understood to one skilled in the art that other milk high in alpha.sub.s2-casein may be suitable for the present invention. Choice of milk may be influenced, inter alia, by economic factors and availability of particular milk. The selection of milk containing high levels of alpha.sub.s2-casein, which is low in alpha.sub.s1-casein, may be carried out by reversed-phase high performance liquid chromatography (RP-HPLC) (Mora-Gutierrez et al. in J. Dairy Sci. 74, 3303-3307 (1991)). The casein composition of the caprine caseinophosphopeptide is normally as follows: alpha.sub.s2-casein content=29.2 wt. %, alpha.sub.s1-casein content=5.9 wt. %; beta-casein content=50.5 wt. % and kappa-casein content=14.4 wt. %.

The fat in caprine (goat) milk is also rich in medium-chain triglycerides (MCT) (C6:0 Caproic, C8:0 Caprylic and C10:0 Capric) which are absorbed in the proximal intestine and do not require bile salts to be absorbed (Vanderhoof et al. in J. Parenter. Enteral Nutr. 8, 685-689 (1984)). These MCT have become of considerable interest to the medical profession because of their unique benefits in many metabolic diseases of humans (Babayan V. K. in J. Amer. Oil Chem. 59, 49A-51A (1981)). The bone (femur and sternum) is the preferential organ for the deposit of magnesium in animals fed a caprine (goat) milk diet, which has been ascribed to its special characteristics concerning lipid composition (rich in MCT) (Lopez-Aliaga et al. in J. Dairy Sci. 86, 2958-2966 (2003)). Lipids are associated with proteins (caseins) in milk and their content in bound lipid fractions is high (Cerbulis J. in J. Agric. Food Chem. 15, 784-786 (1967)). The MCT content of the caprine caseinophosphopeptide used in this inventive antioxidant composition is high because this caprine caseinophosphopeptide is produced from caprine (goat) milk with a fat content of 1 wt. % by enzymatic hydrolysis and acid precipitation with chitosan. Chitosan, which assumes a polycationic character at acidic pH, exhibits a high fat-binding capacity (No et al. in J. Food Sci. 65, 1134-1137 (2000)).

In an exemplary embodiment of the invention, caprine (goat) milk (1% fat content) characterized by a high $\alpha_{s2}$-casein content is used as the starting material in a method of the present invention: (a) digesting the casein present in caprine (goat) milk high in $\alpha_{s2}$-casein with 0.01% (w/v) trypsin (enzymatically modified proteins through trypsin digestion) at a substantially neutral pH to produce a crude caseinophosphopeptide, (b) reducing the pH to 4.5 with 2% (w/v) chitosan (SEACURE L 110 with 70 wt. % deacetylation; Pronova Biopolymer, Inc., Oslo, Norway) dissolved in 10% citric acid (w/v), (c) removing the unreacted casein from the supernatant by centrifugation, (d) permitting the supernatant to stand for 20 hours at 4° C., (e) adjusting the pH of the supernatant to about 6.0, then adding calcium chloride (0.2% w/v) and ethanol (40% v/v), to precipitate a calcium-bound caseinophosphopeptide, which is recovered by centrifugation. This calcium-bound caseinophosphopeptide may be washed with deionized water and dried by lyophilization. The composition of the lyophilized product is provided in Table 1.

TABLE 1

| Caprine caseinophosphopeptide composition | Per 100 grams |
| --- | --- |
| Kjeldahl N | 6.49 |
| Calcium | 8.61 |
| Phosphorus | 2.76 |
| Medium-chain triglycerides | 9.71 |

A food grade acidulant may be added to the fat emulsion before adding the acid-soluble caprine caseinophosphopeptide. The acid-soluble caprine caseinophosphopeptide may be added to an acidic environment ranging from approximately pH 2.0 to 5.7. The food grade acidulant may be citric acid, ascorbic acid, gluconic acid, and mixtures thereof. The acidulant in the fat emulsion may be mostly citric acid. Citric acid sequesters deleterious trace metals, particularly copper and iron, which hasten deterioration of color, flavor and vitamin A content.

As used herein, the term LBJ refers to a mixture of sugars and soluble fiber derived from eggplant (*Solanum melongena*). To produce LBJ in one example, whole eggplant is slurried with water to which citric acid and iota-carrageenan are added. This mixture is reacted at elevated temperature under controlled conditions for a specific period of time. The resulting slurry of sugars/soluble fiber (LBJ) is subsequently treated with an adsorptive resin functional to remove from the sugars/soluble fiber (LBJ) bitter taste components, color and odor components. The treated sugars/soluble fiber (LBJ) solution may be concentrated and dried if desired to powder form. The further addition of polyphenols, specifically the polyphenols derived from the fruit of *Solanum melongena* is possible.

More specifically, in an exemplary embodiment, an aqueous solution containing 0.50 wt. % citric acid and 0.25 wt. % iota-carrageenan is heated at 45° C. for 6 hours with continuous stirring. Eggplant samples may be obtained from local food stores or any other source and stored under refrigeration at approximately 4° C. until use if necessary. About one hour prior to use, the eggplant samples are removed from refrigeration and equilibrated at room temperature at about 22° C. The eggplants (0.7 kg) are rinsed with water, peeled and then sliced into 4-5 mm thick slices. These are immediately immersed in a treatment bath containing the mixed-acid solution of citric acid and iota-carrageenan. The treatment bath with the sliced eggplants and mixed-acid solution of citric acid and iota-carrageenan is then heated to a temperature that may be in the range 70° C. to 80° C., typically 75° C. This elevated temperature may be maintained for at least 2 hours but possibly held at such elevated temperature for longer, e.g., about 4 hours, and then cooled to between 0° C. and 50° C., in a particular embodiment about 4° C., for a period of time, typically about 12 hours. Finally, the mixture is decanted through Whatman No. 4 filter paper or similar filtration medium.

In an exemplary embodiment, the aqueous slurry/solution (LBJ) is passed through a column of an adsorptive resin. The adsorptive resin may be a polymeric resin, which functions to remove bitterness, odor and color from the aqueous slurry/solution (LBJ). One suitable class of adsorptive resins for use are polymeric cross-linked resins composed of styrene and divinylbenzene such as, for example, the Amberlite series of resins, e.g., Amberlite XAD-2, Amberlite XAD-4 and Amberlite XAD-16, which are available commercially from Supelco of Bellefonte, Pa. Other polymeric crosslinked styrene and divinylbenzene adsorptive resins suitable for use according to the invention are XFS-4257, XFS-4022, XUS-40323 and XUS-40322 manufactured by Dow Chemical Company of Midland, Mich., and other similar resins.

Treatment of the aqueous slurry/solution (LBJ) in accordance with this invention may be conducted in various manners such as by a batch treatment or by passing the aqueous slurry/solution (LBJ) through a column containing the adsorptive resin. The column size selected depends upon the sample size and the concentration of the aqueous slurry/solution (LBJ).

More specifically, in an exemplary embodiment, a batch of approximately 100 g of Amberlite XAD-2 is slurried in water and poured into an open glass chromatography column (2×30 cm) fitted with a Teflon stopcock. The column is then prepared for use by washing it with two liters of twice-distilled water, two liters of distilled methanol (reagent grade), and finally two liters of distilled water. The aqueous slurry/solution (LBJ) treated in the column may preferably be free of insoluble material so as to not plug the column or impede flow. Generally, the concentration of eggplant undergoing treatment may be in the range of about 50 to 70% by weight. The pH of the slurry/solution (LBJ) may be in the range of pH 3 to 4. The flow rate of the aqueous slurry/solution (LBJ) through the column may preferably be slow enough to allow sufficient time for the undesired bitterness, color and odor to be adsorbed in the adsorptive resin. Column flow rates between one to five bed volumes/hour are generally satisfactory.

One aqueous slurry/solution (LBJ) according to the present invention contains a fructose portion of 3.7 wt. % and a sucrose portion of 1.5 wt. % as determined by high-performance liquid chromatography (HPLC). Thus, this natural composition exhibits a high hygroscopic property. Saccharide polymers may be used as spray-drying aids in the manufacture of this natural composition. The composition may include between around 5 and 10% by weight maltodextrin.

The maltodextrin may have a low DE, generally not exceeding about 10. The aqueous slurry/solution (LBJ) is mixed with maltodextrin DE=10 at a concentration of 6% (by weight) after the aqueous slurry/solution (LBJ) is passed through a column of the adsorptive resin. Then, the aqueous slurry/solution (LBJ 10) is dried by spray drying or the like to provide a product that is well suited for use as a natural antioxidant ingredient for fat emulsions. The composition of this product is provided in Table 2.

TABLE 2

| LBJ 10 physicochemical composition | Per 100 grams |
|---|---|
| carbohydrate portion | 92.21 |
| nitrogen content | 0.71 |
| fat portion | 0.16 |
| ash portion | 2.33 |
| dietary fiber portion | 0.41 |
| soluble fiber portion | 0.41 |
| fructose portion | 3.72 |
| glucose portion | 4.26 |
| sucrose portion | 1.48 |
| maltose portion | 2.19 |
| sugar portion | 11.65 |

The numerical values for carbohydrate, crude protein, fat portion, ash portion, dietary fiber portion, soluble fiber portion, and sugar portion are those according to a general analysis.

Carrageenans exhibit thickening or viscosity-increasing effect. The viscosity of the LBJ 10 composition of Table 2, which has 0.25 wt. % iota-carrageenan, is rather low, i.e., about 11 cps (1%, 22° C.), and it tastes slightly sweet and is odorless. Carrageenans such as kappa-carrageenan and lambda-carrageenan can also be used in the preparation of LBJ 10. Carrageenans are known to interact with casein (and derived phosphopeptides) to modify food texture by improving water holding capacity (Mora-Gutierrez et al. in J. Agric. Food Chem. 46, 4987-4996 (1998)). In some embodiments of the invention, the combination of egg yolk phospholipids, caprine caseinophosphopeptide and LBJ 10 impart richness, lubricity and creaminess to fat-reduced emulsions. Because antioxidant activities are correlated with the phenolic contents of foods, the total phenolic content of LBJ 10 was determined using methods described by Singlenton et al., Analysis of Total Phenols and Other Oxidation Substrates and Antioxidants by Means of Folin-Ciocalteu Reagent, Methods in Enzymology, Oxidants and Antioxidants, 1998, pp. 152-178. The total phenolic content of LBJ 10 was 45 µmol gallic acid equivalents/g of LBJ 10.

The present invention includes compositions of natural antioxidants including tocopherols, beta-carotene, egg yolk or soybean phospholipids, sucrose or sorbitol, caprine caseinophosphopeptide-chitosan complex, eggplant (LBJ 10), and citric acid. Specific antioxidant ingredients of the present invention may include from about 0.01 to about 0.03% by lipid content of tocopherols, from about 0.01 to about 0.03% by lipid content of beta-carotene, from about 0.05 to about 0.5% by weight of emulsion of egg yolk or soybean phospholipids, from about 2 to about 20% by weight of emulsion of sucrose or sorbitol, from about 0.01 to about 0.05% by weight of emulsion of caprine caseinophosphopeptide-chitosan complex, from about 0.01 to about 0.2% by weight of emulsion of eggplant (LBJ 10), and from about 0.01 to about 0.5% by weight of emulsion of citric acid.

One specific composition includes about 0.01% tocopherols, 0.01% beta-carotene, 0.1% egg yolk or soybean phospholipids, 10% sorbitol, about 0.05% caprine caseinophosphopeptide-chitosan complex, about 0.01% eggplant (LBJ 10), and about 0.01% citric acid, all by weight of emulsion.

Unrefined Canadian flaxseed oil is rich in tocopherols and beta-carotene. A specific embodiment of the composition of the present invention, especially effective for O/W emulsions prepared with Canadian flaxseed oil, is as follows: 0.05% caprine caseinophosphopeptide-chitosan complex, 0.01% eggplant (LBJ 10), and 0.01% citric acid by weight of emulsion.

The fat emulsion may be produced by conventional technology. An exemplary production process includes adding egg yolk or soybean phospholipids in suitable amounts to a predetermined amount of the oil component, homogenizing the mixture, adding sorbitol, caprine caseinophosphopeptide-chitosan complex, eggplant (LBJ 10), and citric acid in suitable amounts to a predetermined amount of the water component, and emulsifying the entire mixture with a homogenizing machine such as the conventional homo-mixer, homogenizer, ultrasonic homogenizer, or pressure homogenizer. The mixture may preferably be finely dispersed by homogenization to ensure a homogeneous equal dispersion of the natural antioxidant composition in all the oil particles. The average particle diameter of the fat emulsion particles is within the range of 5-50 nm. The emulsified mixture may be pasteurized using conventional methods.

Some natural antioxidant compositions of the present invention may exhibit antioxidant activity superior to prior compositions or synthetic antioxidants. Some natural antioxidant compositions of the present invention may also offer a number of health benefits, including helping to promote bone health by boosting calcium and magnesium absorption, and a healthy cardiovascular system by lowering blood serum cholesterol levels. Thus in certain embodiments, the amount of caprine caseinophosphopeptide and eggplant (LBJ 10) may range from the minimum amount which will stabilize the oil against oxidation, or effectiveness, to at least that amount which will promote bone health and protect against heart disease in animal or human bodies. In general, the amount of caprine caseinophosphopeptide-chitosan complex and eggplant (LBJ 10) used may range from 0.01 to 0.05% by weight for caprine caseinophosphopeptide-chitosan complex and 0.01% to 0.1% by weight for eggplant (LBJ 10).

Exemplary Data

The procedures utilized for all of the below examples are identical except where explicitly noted. Therefore, only the differences are noted from one example to the next example as indicated in square brackets [ . . . ]. Further, ascorbyl palmitate (0.03% w/w, based on the weight of the oil, is added to oil blend followed by homogenization is only added to pH 6.0 and not pH 3.0 (as it is pro-oxidant at the lower pH values). The ionic emulsifier, egg yolk phospholipids (ω6-PL-85.sup.™), was used in the present oxidative stability studies of O/W Menhaden oil-based emulsions 'blended' with Smart Balance Omega.sup.™ oil (Examples 1 thru 9). All results are within Table 3.

The following examples are included to demonstrate specific embodiments of the invention. It should be appreciated by those of skill in the art that the techniques disclosed in the examples that follow represent techniques discovered by the inventors to function well in the practice of the invention.

However, those of skill in the art should, in light of the present disclosure, appreciate that many changes can be made in the specific embodiments that are disclosed and still obtain a like or similar result without departing from the spirit and scope of the invention.

Examples 1 through 9 demonstrate Omega-3 emulsions with a range of synergistic actives.

The health benefits of some embodiments of the present invention are explained in detail in Examples 10 through 12.

EXAMPLE 1=25% O/W Menhaden/Smart Blend Omega Emulsions (pH 6.0) Containing Caprine CPP-Chitosan Complex and Food-Grade EDTA (ethylenediaminetetraacetate)

A=Control

Menhaden oil/Smart Blend Omega oil at 1:1 ratio (25%) is homogenized with egg yolk phospholipids "rich" in PC (0.3% w/w, based on the weight of the oil) followed by homogenization, then Cavamax CoQ10.sup.™ (0.3% w/w, based on the weight of the emulsion) is added to this oil blend followed by homogenization. An aqueous solution (75% of double deionized water) containing potassium phosphate monobasic (0.01% w/w, based on the weight of the emulsion), mannitol (4% w/w, based on the weight of the emulsion) and trehalose (2% w/w, based on the weight of the emulsion) is stirred. [The pH of this aqueous solution (water phase) is adjusted to 6.0 with 0.1 N potassium hydroxide (KOH)]. The emulsified oil blend (25%) is added to the aqueous solution (75%) followed by homogenization.

B=Treatment

Menhaden oil/Smart Blend Omega oil at 1:1 ratio (25%) is homogenized with egg yolk phospholipids "rich" in PC (0.3% w/w, based on the weight of the oil), then Cavamax CoQ10.sup.™ (0.3% w/w, based on the weight of the oil) is added to this oil blend followed by homogenization. [Ascorbyl palmitate (0.03% w/w, based on the weight of the oil, is added to oil blend followed by homogenization.] An aqueous solution (75% of double deionized water) containing potassium phosphate monobasic (0.01% w/w, based on the weight of the emulsion), mannitol (4% w/w, based on the weight of the emulsion) and trehalose (2% w/w, based on the weight of the emulsion) is stirred. Gallic acid (0.002% w/w, based on the weight of the emulsion) and [Ca-EDTA (0.0070% w/w, based on the weight of the oil) are added and stirred. The pH of this aqueous solution (water phase) is adjusted to 6.0 with 0.1 N potassium hydroxide (KOH)]. Caprine CPP-chitosan complex (0.04% w/w, based on the weight of the emulsion) is added to this aqueous solution and homogenized. The emulsified oil (negatively charged oil phase) (25%) is added to this aqueous solution (positively charged water phase) (75%) followed by homogenization.

Samples were stored in 50 ml capped, sterile brown glass bottles in an incubator for 28 days at 40° C., and, samples were taken at 14 and 28 days. Samples were analyzed for the peroxide value (hydroperoxides) and p-anisadine value (aldehydes). The antioxidant activity of the composition according to an embodiment of the present invention is demonstrated below.

EXAMPLE 2=25% O/W Menhaden/Smart Blend Omega Emulsions (pH 6.0) Containing Caprine CPP-Chitosan Complex and Phytic Acid B=Treatment

[and phytic acid (0.3% w/w, based on the weight of the emulsion) are added and stirred. The pH of this aqueous solution (water phase) is adjusted to 6.0 with 0.1 N potassium hydroxide (KOH)].

EXAMPLE 3=25% O/W Menhaden/Smart Blend Omega Emulsions (pH 3.0) Containing Caprine CPP-Chitosan Complex and Food-Grade EDTA (ethylenediaminetetraacetate)

A=Control

[The pH of this aqueous solution (water phase) is adjusted to 3.0 with 10 mM lactic acid.]

B=Treatment

No ascorbyl palmitate. [The pH of this aqueous solution (water phase) is adjusted to 3.0 with 10 mM lactic acid. Gallic acid (0.002% w/w, based on the weight of the emulsion) and Ca-EDTA (0.007% w/w, based on the weight of the oil) are added and stirred. Gallic acid is acidic. Thus, the pH of this aqueous solution (water phase) should be re-adjusted to 3.0 with 0.1 N potassium hydroxide (KOH)].

EXAMPLE 4=25% O/W Menhaden/Smart Blend Omega Emulsions (pH 3.0) Containing Caprine CPP-Chitosan Complex and Phytic Acid A=Control

[The pH of this aqueous solution (water phase) is adjusted to 3.0 with 10 mM lactic acid.]

B=Treatment

No ascorbyl palmitate. [The pH of this aqueous solution (water phase) is adjusted to 3.0 with 10 mM lactic acid. Gallic acid (0.002% w/w, based on the weight of the emulsion) and phytic acid(0.3% w/w, based on the weight of the emulsion) are added and stirred. Gallic acid is acidic. Thus, the pH of this aqueous solution (water phase) should be re-adjusted to 3.0 with 0.1 N potassium hydroxide (KOH)].

EXAMPLE 5=25% O/W Menhaden/Smart Blend Omega Emulsions (pH 3.0) Containing Caprine CPP-Chitosan Complex and Lactoferrin A=Control

[The pH of this aqueous solution (water phase) is adjusted to 3.0 with 10 mM lactic acid.]

B=Treatment

No ascorbyl palmitate. [The pH of this aqueous solution (water phase) is adjusted to 3.0 with 10 mM lactic acid. Gallic acid (0.002% w/w, based on the weight of the emulsion) and lactoferrin (0.01% w/w, based on the weight of the emulsion) are added and stirred. Gallic acid is acidic. Thus, the pH of this aqueous solution (water phase) should be re-adjusted to 3.0 with 0.1 N potassium hydroxide (KOH)].

EXAMPLE 6=25% O/W Menhaden/Smart Blend Omega Emulsions (pH 3.0) Containing Caprine CPP-Chitosan Complex, Lactoferrin and Grape Seed Extract A=Control
[The pH of this aqueous solution (water phase) is adjusted to 3.0 with 10 mM lactic acid.]
B=Treatment
No ascorbyl palmitate. [The pH of this aqueous solution (water phase) is adjusted to 3.0 with 10 mM lactic acid. Grape seed extract (0.01% w/w, based on the weight of the emulsion) and lactoferrin (0.01% w/w, based on the weight of the emulsion) are added and stirred].

EXAMPLE 7=25% O/W Menhaden/Smart Blend Omega Emulsions (pH 3.0) Containing Caprine CPP-Chitosan Complex, Lactoferrin and Resveratrol A=Control
[The pH of this aqueous solution (water phase) is adjusted to 3.0 with 10 mM lactic acid.]
B=Treatment
No ascorbyl palmitate. [The pH of this aqueous solution (water phase) is adjusted to 3.0 with 10 mM lactic acid. Resveratrol (0.01% w/w, based on the weight of the emulsion) and lactoferrin (0.01% w/w, based on the weight of the emulsion) are added and stirred].

EXAMPLE 8=25% O/W Menhaden/Smart Blend Omega Emulsions (pH 6.0) Containing Caprine CPP-Chitosan Complex, Food-Grade EDTA (ethylenediaminetetraacetate) and New Zealand Wool-Derived Keratine (Cynatine FLX™)

A=Control
B=Treatment
[New Zealand wool-derived keratine (Cynatine FLX™) are added to this aqueous solution (pH 6.0) and homogenized.]

EXAMPLE 9=25% O/W Menhaden/Smart Blend Omega Emulsions (pH 3.0) Containing Caprine CPP-Chitosan Complex, Food-Grade EDTA (ethylenediaminetetraacetate) and New Zealand Wool-Derived Keratine (Cynatine FLX.sup.™)

A=Control
[The pH of this aqueous solution (water phase) is adjusted to 3.0 with 10 mM lactic acid.]
B=Treatment
No ascorbyl palmitate. [The pH of this aqueous solution (water phase) is adjusted to 3.0 with 10 mM lactic acid. Gallic acid (0.002% w/w, based on the weight of the emulsion) and Ca-EDTA (0.007% w/w, based on the weight of the oil) are added and stirred.] [New Zealand wool-derived keratine (Cynatine FLX.sup.™) are added to this aqueous solution (pH 3.0) and homogenized.]

TABLE 3

| Sample | 14 days peroxide value | 14 days anisidine value | 28 days peroxide value | 28 days anisidine value |
| --- | --- | --- | --- | --- |
| 1A | 4.8 mequiv/kg | 10.7 | 9.2 mequiv/kg | 16.5 |
| 1B | 1.5 mequiv/kg | 4.3 | 3.3 mequiv/kg | 7.1 |
| 2A | 4.9 mequiv/kg | 10.5 | 9.0 mequiv/kg | 16.1 |
| 2B | 3.0 mequiv/kg | 6.7 | 5.7 mequiv/kg | 10.3 |
| 3A | 3.5 mequiv/kg | 6.9 | 8.1 mequiv/kg | 12.6 |
| 3B | 0.9 mequiv/kg | 3.9 | 1.5 mequiv/kg | 5.8 |
| 4A | 3.7 mequiv/kg | 6.9 | 8.0 mequiv/kg | 12.7 |
| 4B | 2.4 mequiv/kg | 4.7 | 5.1 mequiv/kg | 8.3 |
| 5A | 3.9 mequiv/kg | 7.0 | 8.3 mequiv/kg | 12.3 |
| 5B | 2.7 mequiv/kg | 4.8 | 5.8 mequiv/kg | 8.6 |
| 6A | 3.9 mequiv/kg | 6.9 | 8.3 mequiv/kg | 12.3 |
| 6B | 2.6 mequiv/kg | 4.8 | 5.6 mequiv/kg | 8.5 |
| 7A | 3.9 mequiv/kg | 7.0 | 8.3 mequiv/kg | 12.3 |
| 7B | 2.7 mequiv/kg | 4.9 | 5.5 mequiv/kg | 8.6 |
| 8A | 4.8 mequiv/kg | 10.7 | 9.2 mequiv/kg | 16.5 |
| 8B | 1.3 mequiv/kg | 4.1 | 3.2 mequiv/kg | 7.0 |
| 9A | 3.5 mequiv/kg | 6.9 | 8.1 mequiv/kg | 12.6 |
| 9B | 1.1 mequiv/kg | 4.0 | 1.4 mequiv/kg | 5.5 |

EXAMPLE 10

Cholesterol-Lowering Activity in Rats

Rats (Sprague-Dawley type, 7 weeks of age, male) were fed a diet low in calcium and high in animal fat. These rats were divided into three groups each being formed of 12 rats having a similar mean body weight of 200-205 grams, then three kinds of heat-sterilized O/W nanoemulsions i.e., an O/W nanoemulsion of 0.05% (w/v) caprine caseinophosphopeptide-chitosan complex and 0.01% (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). Blood collection was carried out from cardiac puncture. With respect to analysis, measurements were carried out using a DU-530 Spectrophotometer made by Beckman by means of a colorimetric method.

Results of the measurement for blood serum total cholesterol are shown in Table 4.

TABLE 4

| Group | Cholesterol, mg/dL |
| --- | --- |
| Control (non-supplemented) | 84.92 ± 7 |
| Control (supplemented) | 78.36 ± 5 |
| Natural antioxidant composition (supplemented) | 67.30 ± 4 |

According to the above results, it has been proved that the increase in serum cholesterol of male Sprague-Dawley rats fed a low calcium and high animal fat diet has been lowered by the addition of an antioxidant composition according to an embodiment of the present invention (caprine caseinophosphopeptide-chitosan complex combined with eggplant (LBJ 10) and citric acid at levels of 0.05% (w/v), 0.01% (w/v), and 0.5% (w/v), respectively) to a calcium-supplemented O/W emulsion.

This natural antioxidant composition, therefore, can be applied to O/W nanoemulsions as physiologically functional factor.

EXAMPLE 11

Calcium and Magnesium Bioavailability in Rats

Rats (Sprague-Dawley type, 7 weeks of age, male) were fed an egg white-diet low in calcium. Chromic oxide ($Cr_2O_3$, 0.5 g/kg diet), an insoluble and unabsorbed marker, was added to the egg white-diet to allow estimation of apparent Ca and Mg absorption by determining the ratio of Ca:Cr and Mg:Cr in the diet and feces. These rats were divided into four groups each being formed of 12 rats and having a similar mean body weight of 200-205 grams, then three kinds of heat-sterilized O/W nanoemulsions i.e., an O/W nanoemulsion of 0.05% (w/v) caprine caseinophosphopeptide-chitosan complex and 0.01% (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. Food intake was measured every day. Feces were collected during the last 3 days and freeze-dried. At the end of the 21-day, rats were deprived of food overnight and anesthetized by intraperitoneal injection of sodium pentobarbital (40 mg/kg body weight). The right femurs were excised for measurement of Ca, and Mg content. The amounts of Ca, Mg, and Cr in the diets and feces were quantified by atomic absorption spectrometry (Varian Analytical Instruments, Walnut Creek, Calif., USA) after wet-washing with an acid mixture (16 mol/L $HNO_3$:9 mol/L $HClO_4$=3:1). The right femurs were treated with 1N $HNO_3$ and ashed at 550 degrees C. Ca and Mg content were determined in the same manner as in the case of the diets and feces. Apparent Ca absorption was calculated by the following formula: Apparent Ca absorption (%)=100[(Ca intake/Cr intake)−(Ca in the feces/Cr in the feces)]/(Ca intake/Cr intake). Apparent Mg absorption was calculated in a similar manner.

The apparent Ca and Mg absorption, and femoral bone Ca and Mg content of rats fed the three different O/W nanoemulsions are shown in Table 5.

The data show enhanced Ca and Mg bioavailability from the O/W nanoemulsion containing an antioxidant composition according to an embodiment of the present invention.

EXAMPLE 12

Bone Metabolism and Dynamic Strength of Bone in Rats

Rats (Sprague-Dawley type, 7 weeks of age, male) were fed a diet low in calcium. These rats were divided into four groups each being formed of 12 rats and having a similar mean body weight of 200-205 grams, then three kinds of heat-sterilized O/W nanoemulsions i.e., an O/W nanoemulsion of 0.05% (w/v) caprine caseinophosphopeptide-chitosan complex and 0.01% (w/v) eggplant (LBJ 10) supplemented with calcium (300 ppm), an O/W nanoemulsion supplemented with calcium (300 ppm), and an O/W nanoemulsion non-supplemented with calcium were respectively given from feeding bottles to the rats as drinking water. Composition of these O/W nanoemulsions was identical in terms of flaxseed oil (1 g/L), soybean phospholipids (0.1 g/L), sucrose (4 g/L), and citric acid (5.0 g/L) content. O/W nanoemulsions were supplemented with calcium gluconate (3 g/L).

The three groups of rats were free to take the feed and water in, during the treatment period of 21 days. At the end of the 21-day, rats were deprived of food overnight and anesthetized by intraperitoneal injection of sodium pentobarbital (40 mg/kg body weight). The left femurs were collected from the animals and soft tissue was removed. The left femur from each animal was subjected to bone mineral content (BMC), bone mineral density (BMD), and bone mechanical strength (BMS) measurements using dual-energy X-ray absorptiometry (DEXA), which is a typical method used to study the status of bone growth. Table 6 shows the beneficial effects of an antioxidant composition according to an embodiment of the present invention on bone metabolism and dynamic strength of bone in rats.

TABLE 6

| Group | BMC (g) | BMD (g/cm2) | BMS (kg force) |
|---|---|---|---|
| Control (non-supplemented) | 0.1912 ± 0.012 | 0.1346 ± 0.004 | 8.402 ± 0.321 |
| Control (supplemented) | 0.2041 ± 0.012 | 0.1432 ± 0.004 | 8.591 ± 0.298 |
| Antioxidant composition (supplemented) | 0.2134 ± 0.012 | 0.1518 ± 0.004 | 9.567 ± 0.298 |

The data clearly indicate that the O/W nanoemulsion containing an antioxidant composition according to an embodiment of the present invention strengthens the femur bones in

TABLE 5

| Group | Apparent Ca absorption (%) | Apparent Mg absorption (%) | Bone Ca content (mg/femur) | Bone Mg content (mg/femur) |
|---|---|---|---|---|
| Control (non-supplemented | 49 ± 5.7 | 51 ± 4.2 | 89.63 ± 0.27 | 4.47 ± 0.13 |
| Control (supplemented) | 54 ± 6.0 | 49 ± 5.1 | 97.08 ± 0.19 | 4.31 ± 0.27 |
| Antioxidant Composition (supplemented) | 59 ± 5.0 | 61 ± 5.9 | 103.20 ± 0.14 | 5.62 ± 0.11 | rats by enhancing the amount of magnesium retained in bone (Example 11), and that this results from increased apparent magnesium absorption (Example 11).

The caprine caseinophosphopeptide-chitosan-MCT bound complexes, which are present in the above antioxidant composition according to an embodiment of the present invention, are thermally stable and deliver large amount of magnesium to the proximal intestine, the site for magnesium absorption. Thus the complexes per se can provide physiological activity of magnesium to low-pH, protein-based beverages and transparent beverages processed by heat treatment. The complexes prevent protein sedimentation in low pH (3.5-4.2) beverages when used in combination with high-methoxyl pectins or pectin alginates.

EXAMPLE 13

Transparent Low-pH (3.0-4.2) Beverages Containing Caprine Caseinophosphopeptide

A big factor in the drop in calcium and magnesium consumption in the United States is the fact that soft drinks have replaced milk in the American diet. Milk is an excellent source of calcium (1,310 mg/L) and also contains magnesium (120 mg/L). A Consumer Beverage Consumption study conducted in late 2000, surveyed a total of 1,379 participants in two age groups-adults (19-64; 320 males/358 females) and teens (12-18; 326 boys/375 girls). Adults reported that their favorite beverage is "cold, refreshing, and satisfying" whereas teens prefer their drinks to be "cold, refreshing, and delicious". In this survey, teens and adults, milk drinkers and non-milk drinkers expressed comments regarding their concern with health issues, additives, chemicals, handling and spoilage.

A growing body of research now shows that the more soft drinks teenagers consume, the higher their risk of broken bones and, in later life, osteoporosis. Since 1970 Americans have more than doubled their soft drink consumption while drinking less milk. Consumers want a cold, refreshing, satisfying, portable, and healthy beverage. Caprine caseinophosphopeptide-chitosan complex can be used in transparent low-pH (3.0-4.2) beverages fortified with calcium and magnesium to prevent the loss of these minerals from bone and therefore, lowering the risk of bone fractures.

Caprine caseinophosphopeptide-chitosan complex can also form the building stones for mineral-fortified, low-pH beverages tailored for individuals with lactase non-persistence, a reduced capacity to metabolize lactose. The presence of lactose in milk is detrimental for those individuals that suffer from lactose intolerance. The ingestion of one to two glasses of milk can lead to abdominal discomfort and diarrhea in such individuals. Many studies have noted racial differences in the incidence of lactose intolerance. In the United States is estimated that only 10-15% of adult Caucasians react adversely to lactose, whereas 70% of adult Afro-Americans are lactose intolerance. The incidence of lactose intolerance in adult Asians is 95%. The beverage food industry could formulate a calcium- and magnesium-fortified beverage containing caprine caseinophosphopeptide-chitosan complex to export to the Far East.

EXAMPLE 14

Coated Nuts

Long shunned by dieters for their fat content, nuts have made a big-time dietary come back. Recent epidemiological studies suggest that frequent nut consumption may be protective against heart disease and other chronic diseases. As mentioned earlier, the level of fat in the diet influences magnesium absorption because fatty acids have a greater tendency to form soaps with calcium than magnesium (Van Dokkun et al. in Ann. Nutr. Metab. 27, 361-367 (1983)).

Recent research studies have shown that increased lipid proportion of the diet improves the digestive utilization of magnesium in clinical cases of malabsorption syndrome (Alférez et al. in J. Dairy Res. 68, 451-461 (2001)). Increased proportions of protein in the diet also favor magnesium absorption (Pallarés et al. in J. Agric. Food Chem. 44, 1816-1820 (1996)). Nuts are rich in fat, protein, and magnesium. The inventive antioxidant composition promotes a significant increase of magnesium absorption, which is reflected in the greater quantity of this mineral stored in femoral bone. Magnesium is associated with strong bones. People who crunch on nuts coated with the inventive antioxidant composition can lower the risk of bone fractures.

The further addition of coenzyme Q10 also enhances the antioxidative stability of lipids, including within the inventive nanoemulsions. The more preferred coenzyme Q10 is infused into the oil phase prior to emulsion. The particularly preferred coenzyme Q10 is modified through means known in the art, such as "encapsulation" into gamma-cyclodextrin provided by Wacker in their Cavamax CoQ10.sup.™ product, to be solubilized in the oil phase of the emulsion. The amount of coenzyme Q10 within the oil phase can range from 0.25% to 5% of the oil on a w/w basis. The preferred amount of coenzyme Q10 is within the range of 0.25% to 1.25%. The more preferred amount of the coenzyme Q10 is within the range of 0.25% to 1.0%. The presence of coenzyme Q10 in essentially any amount, including trace amounts, yields superior antioxidative stability of the lipid phase. The further ability of to regenerate oxidized forms of Vitamin E and glutathione by coenzyme Q10 is a further synergistic benefit of the combination of glutathione and coenzyme Q10.

The resulting testing has both expanded the range of acceptable pH modifiers (and the range of suitable pH from 2.8 to 6.6) and in fact has lead to the more preferred pH modifiers now including gallic acid, fumaric acid, pantothenic acid, and choline citrate. The combination of the preferred pH modifiers has a synergistic effect in terms of oxidative stability with the further inclusion of electron transfer mediators such as potassium hydroxide, calcium hydroxide, and magnesium hydroxide. The role of said electron transfer mediators has been further elucidated as a superior understanding of the theory explaining the significant gains in antioxidative stability being largely attributed to the creation of an electron transfer bridge at the interface of the oil and water phases of emulsions in general and particularly in the more susceptible nanoemulsions.

Additional more preferred polyols now include trehalose. The combinations of trehalose with the noted electron transfer mediators yield superior oxidative stability. Trehalose has the secondary advantage of protecting proteins (and derived peptides), an important benefit in providing enhanced antioxidative stability when the protein and/or peptide is exposed to elevated temperatures and/or when the emulsion is dried. In addition to the protein stabilizer trehalose, polyethylene glycol (PEG) can be added to the emulsion prior to drying. PEG provides surface modification of the protein and/or peptide. Thus the utilization, without being bound by theory, of trehalose and/or PEG provides further encapsulation of the lipid phase within the micelles.

Additional more preferred phospholipids includes phospholipids rich in phosphatidylcholine (PC). Rich is contextually defined as being of greater than 40% on a weight basis. Thus the preferred formulation is the inclusion of PC rich phospholipids into the oil phase during emulsification. An important integral component of the inventive bioactive complex is the electrostatic interactions of the polycationic milk peptide-chitosan complex with negatively charged bilayers, such as PC rich phospholipids. The combination markedly reduces the fluid spacing between the negatively charged lipid bilayers. These bridges are stabilized by increased adhesion arising from increased van der Waals interactions between the opposing bilayers, electrostatic interactions between the pi electrons in the phenol ring (e.g., tocopherols) and the—$(N^+CH_3)_3$ groups on the PC headgroups, decreased hydration repulsion between bilayers, and hydrogen bonds between the H-bond-donating moieties on the polyphenols, particularly tocopherols, and H-bond-accepting groups n the bilayer. The increased bilayer adhesion is essential for enhanced oxidative stability of emulsions.

One exemplary formulation procedure is the homogenization of Omega Pure.sup.™ Menhaden fish oil (25%) for 4 minutes with egg yolk phospholipids "rich" in PC at 0.2% w/w (Sigma Chemical 60% PC) based on the weight of the fish oil, then 0.25% gamma-cyclodextrin encapsulated coenzyme Q10 (w/w, based on the weight of the fish oil) is added with subsequent homogenization for 4 minutes. An aqueous solution (75% of double deionized water) containing mannitol (4% w/w/, based on the weight of the emulsion) and trehalose (2% w/w, based on the weight of the emulsion) is magnetically stirred for 4 minutes. Gallic acid (0.002% w/w, based on the weight of the emulsion) is subsequently added and magnetically stirred for 2 minutes. The pH of this aqueous solution (water phase) is adjusted to pH 6.0 with the preferred electron transfer mediator of potassium hydroxide 0.1 N (alternatively/preferably a combination of KOH and choline citrate is used). The earlier prepared caprine casein phosphopeptide-chitosan complex (0.04% w/w, based on the weight of the emulsion) is added to this aqueous solution and homogenized for 1 minute. The oil phase and aqueous phase are combined and homogenized for 4 minutes (production methods would include multiple pass high pressure homogenization) resulting into an oil in water emulsion. Without being bound by theory, the resulting micelles at the interface between the oil and water phase contain an iron-sulfur cluster as a means to provide an electron transfer bridge across the two phases.

Additional more preferred casein phosphopeptides are complexed with additional minerals including, though not limited to, magnesium, manganese, selenium, zinc, and iron. The particularly preferred mineral is in the lactate form. And the specifically preferred mineral is zinc lactate. Zinc has secondary advantages associated with protection of RNA and DNA, while calcium has secondary advantages associated with the many health benefits as known in the art for calcium including bone building, and cholesterol reduction.

Additional preferred proteins include keratin and canola, and fragments thereof of keratin and canola protein isolates. More preferred proteins include phosphopeptides of keratin and canola proteins. A supplier of keratin includes Keratec of New Zealand with the preferred product being their Keratec IFP.sup.™, a purified protein fraction isolated from pure New Zealand wool. The Keratec Pep product has a high proportion of cystine derived amino acids as part of the peptide backbone. The particularly preferred Keratec product is Cynatine FLX.sup.™. A supplier of canola protein isolates includes Burcon of Canada in the form of Puratein.sup.™ and Supertein.sup.™.

Additional emulsifiers include the utilization of non-ionic emulsifiers such that the polycationic charge created by the chitosan is not "bound" by the emulsifier.

Additional antioxidants include vanillin, bee propolis, grape seed extract, grape pomace extract, quercitin, carotenoids, and lactoferrin. A preferred antioxidant has reducing sugars eliminated from the antioxidant. Numerous methods exist as known in the art, including the enzymatic elimination of sugars such as glucoseoxidase. Lactoferrin, a recognized powerful antioxidant, provides a synergistic impact of binding otherwise pro-oxidant iron, thus without being bound by theory effectively removes the catalytic iron while providing the inherent antioxidant benefits.

Transparent Beverage

Chitosan is recognized in the art as a means to enhance the intestinal absorption of calcium (Ca) in mammals. Magnesium (Mg) is also recognized as a means to increase bone strength in mammals whereas calcium is known to increase bone density in mammals. However, high dietary Ca/Mg ratios interfere with Mg absorption, because Ca and Mg share common intestinal absorption pathways (Thebault et al. in Adv. Chronic Kidney Dis. 13, 110-117 (2006)). When Ca is elevated with respect to Mg, Ca out-competes Mg for the absorption pathways and hypomagnesaemia (low magnesium in the blood) results. With respect to calcium absorption in humans, it has been shown that bovine CPP administration (87.5 mg) leads to significantly better absorption of co-ingested calcium (250 mg) in normal post-menopausal women with low calcium absorption values (n=17), as determined using an intrinsic Ca label in the calcium source, at a CPP:Ca ratio of 0.35 (Heaney et al. in Bone Miner. Met. 12, 77-81, (1994)). These findings suggest that CPP supplementation is particularly useful for persons with a low basal absorptive performance. This profile of action is fortunate in that it is precisely in such persons with poor absorption that enhancement is needed. Note: 87.5 mg CPP/250 mg Ca=0.35 (CPP/Ca ratio).

In order to overcome this competing scenario between Ca and Mg, the preferred embodiment is comprised of caprine CPP, which is "rich" in medium chain triglycerides "MCT". MCT favors the absorption of magnesium. The more preferred embodiment is comprised of both chitosan and caprine CPP as the synergistic combination achieves results greater than the individual components. Without being bound by theory, the chitosan provides both superior bioadhesion within the GI tract and protects the caprine CPP for a longer period of time against enzymatic degradation of the peptide. The result is superior absorption of both Ca and Mg. The lipid composition rich in MCT and vitamin D both favor the absorption and deposit of magnesium in the femur. Caprine CPP is also high in amino acid lysine that is partially responsible for higher absorption of divalent cations in laboratory animals as compared to bovine milk. Similar results are anticipated from bovine sources of casein that are all characterized by high levels of alphas1-casein (bovine casein is characterized by low or intermediate amounts of alphas2-casein but not high alphas2-casein). Another embodiment is the synergistic combination of chitosan and GPC, which without being bound by theory binds minerals, in particular calcium ions, because of the combined phosphate groups in GPC and bioadhesion and chelating properties of chitosan. Yet another embodiment is caprine CPP-chitosan complex with egg yolk phospholipids (negatively charged) having phosphate groups.

The dietary deficiency of minerals within the normal consumption of food and beverage products is placing new demands on creating new methods for efficiently delivering meaningful minerals supplementation. However, meaningful levels often create taste, clarity, and bioavailability constraints. One such exemplary is the demand for transparent beverage systems meeting the requirement of "excellent source" as defined by the FDA (i.e., 20% of RDA per serving).

One embodiment to achieve a transparent beverage is achieved by the acid precipitation of casein into small peptides (CPP) with the addition of acids such as HCl, citric acid, phytic acid, lactic acid, malic acid, etc. One exemplary preparation is achieved by mixing 2% (w/v) chitosan with 10% (w/v) citric acid prior to the addition into goat's milk. The selection of caprine milk vs. bovine milk achieves superior transparency. Virtually any protein is a candidate for salting-in in the presence of high concentrations of mineral salts, though milk proteins (e.g., casein, whey) and their derived peptides are superior. Several amino acids also bind mineral salts, though to a lower extent than protein hydrolyzates. The salting-in process of caprine CPP with TruCal.sup.™ can be achieved without the inclusion of chitosan. The preferred embodiment is further comprised of a phosphate buffering agent, such as monobasic potassium phosphate. The preferred acids are comprised of at least one acid selected from the group consisting of citric acid, phytic acid, gallic acid and lactic acid. Citric acid is of particular significance because of both its lack of contributing to an in vivo acidic environment, and the recognized within the art interaction with phytic acid as a means to reduce arterial plaque. Phytic acid is of particular significance because of the prior mentioned interaction with citric acid, it's recognized in the art debittering of potassium, and it's excellent chelating power. The novel combination of citric acid, phytic acid, and mineral salts selected from the group of potassium, calcium, magnesium, and zinc with the method of salting-in yields a highly bioavailable, good tasting, and transparent beverage. Gallic acid is of particular significance because of its antioxidant capacity, which is of particular importance as a means to reduce the oxidized cholesterol responsible for the plaque build up. Lactic acid is of particular significance because of the electron donor capacity, which has particular importance when the beverage is comprised of oxidation sensitive oils including Omega-3 rich oils, borage oil, etc. Prior art of an oral chelator (U.S. Pat. No. 7,009,067 by Coppolino on Mar. 7, 2006 titled "Hexa-citrated phytate and process of preparation thereof") claims to dissolve artery plaque and removes excess copper, zinc, and iron deposits in the brain tissue to treat age-related degenerative disorders, such as Alzheimer's disease. The Coppolino complex is one of hexa-citrated phytate based on the steps of slowly adding sufficient amount of calcium carbonate in increments to aqueous phytic acid. Coppolino's invention is inferior to the inventive preferred embodiment of a calcium or magnesium salt (excluding carbonate, and preferably lactate) due in part to lower solubility and bioavailability of calcium carbonate, antioxidant capacity, poor taste, and lack of transparency. A particularly preferred embodiment is a complex comprised of gallic acid (or green tea extract), magnesium lactate, phytic acid, and monobasic potassium phosphate. A more specifically preferred complex is further comprised of at least one selected from the group consisting of chitosan, GPC 85.sup.™, egg yolk PC (Omega 6-PL-85.sup.™), caprine CPP, trehalose and ribose. Without being bound by theory, the chitosan provides superior bioadhesion and chelating, the gallic acid provides superior antioxidant capacity, the magnesium lactate provides both a source of magnesium and lactic acid for electron donor capacity, the phytic acid is an excellent chelating agent, and monobasic potassium phosphate provides both the electrolyte capacity of potassium, and the necessary phosphates. GPC 85.sup.™ and egg yolk PC ((Omega 6-PL-85.sup.™), are both permeation enhancers and orthomolecular. Caprine CPP enhances mineral transport and bioavailability. And trehalose and ribose enhance hydration of the resulting complex. The yet further inclusion of potassium salts in combination with the phytic acid concurrently enhances the electrolyte content, the debittering of the potassium, and the synergistic impact in achieving a highly functional transparent beverage. The superior process method further includes the salting-in of said minerals and acids.

The significant deficiency of magnesium deficiency in the diet is recognized in the art as a means to prevent calcium from being deposited in bones, impair kidney, adrenal, heart, brain, muscle and digestive function, compromises nerve transmissions, restrict carbohydrate metabolism, inhibit the activities of "B" vitamins, retard new cell growth, slow the production of DNA, and so on. One of magnesium's most important duties is the formation of ATP, which is the molecule that provides the energy for virtually everything that occurs within the cells. When we lack magnesium, ATP becomes scarce, metabolism slows, homeostasis becomes more difficult to maintain, stress takes ever greater tolls, and fatigue sets in. An oral chelator comprised of at least one magnesium salt is superior to an oral chelator void of magnesium, as arterial plaque is a function of numerous dietary and health deficiencies. Many of these deficiencies result from blood that is too acid, and the epidemic proportions of diabetes and obesity, all of which magnesium and potassium will provide health benefits. The further combination with phytic acid, which is recognized in U.S. Pat. No. 4,952,568 to Sawai et al. directed to methods for treating type II diabetes by administering phytic acid salts in amounts sufficient to moderate blood glucose levels to foods may be used to delay starch digestion and glycemic response, is more synergistic with magnesium as compared to calcium having the opposite effect. By virtue of their polyoxy nature, many sugar alcohols (i.e., mannitol) form interesting although chemically weak complexes with several polyvalent cations. For various physiologic and nutritional purposes the complexes with calcium, iron, copper and possibly several trace elements in general are important (Knuuttila et al. in Bone & Mineral 6:25-31 (1989)). Trehalose obtained from Cargill Food & Pharma Specialties is known to enhance the absorption of calcium perhaps related to the same mechanism ascribed to the polyols (Yoshizane et al. in U.S. Pat. No. 6,440,446 (2002)). Trehalose is an osmolyte (polyols also exhibit an "osmotically" active nature). Non-reducing sugars such as sucrose, sorbitol and mannitol are known to "chelate" minerals. Ribose is recognized as a key building block to DNA and RNA.

Another embodiment of producing a transparent beverage is comprised of sequential steps of adding a buffering agent, followed by the addition of an acid, then addition of protein complex, then addition of incremental amounts of minerals in combination with further addition of acid until the earlier of failure to eliminate cloudiness or achieving desired level of mineral inclusion. The preferred buffering agent is monobasic potassium phosphate, which has the secondary benefit of being a potassium source. The preferred protein is a hydrolyzed protein (peptide) having enhanced solubility. The particularly preferred protein is further complexed with at least one selected from the group of chitosan, egg yolk PC (Omega 6-PL-85.sup.™), and GPC 85.sup.™. The specifically preferred peptide complex is caprine caseinophosphopeptide (CPP) complexed with chitosan (CPP-chitosan complex). Without being bound by theory, the selection of caprine CPP chitosan complex provides superior bioavailability of minerals, specifically zinc and magnesium in addition to calcium. The preferred acid includes acids selected from the group consisting of gallic acid, malic acid, citric acid, lactic acid, glutamic acid, gluconic acid, and phytic acid. The preferred minerals are comprised of calcium salts, magnesium salts, zinc salts and potassium salts. Particularly preferred minerals are obtained from dairy milk that contains the natural balance of calcium, phosphorous, magnesium and additional trace minerals. The inventive transparent beverage utilizes TruCal.sup.™ obtained from Glanbia Foods (Twin Falls, Id., USA). It is fundamentally important to recognize in the formulation of any food system that calcium loss can take place from too much acid in the diet, which then demands means to increase blood alkanity. A preferred pH adjuster for transparent beverages is therefore citric acid (i.e., calcium citrate) due to its in vivo acid neutralizing impact. This preference for citric acid, however, does not exist when high levels of emulsified oils are present within the beverage, as citric acid induces phase separation.

An important and recognized means to reduce in vivo acidity is through the inclusion of potassium. A preferred embodiment of reducing the bitterness and metallic notes associated with potassium salts (and also zinc salts) respectively is the sequential addition of zinc or potassium salts preceding the subsequent addition of other salts including calcium and magnesium salts. The selection of zinc including zinc sulfate has significant health and nutritional benefits, which when complexed with caprine CPP-chitosan yields superior bioavailability and enzymatic inhibition protecting the peptide in vivo, without being bound by theory, for sustained transport of minerals across the gastrointestinal barrier. Preferred potassium salts are potassium phytate, recognized as a means to reduce the metallic notes of potassium.

The above sequential steps required for salting-in the minerals is a process significantly more time consuming and complex as compared to the traditional adding then mixing in of ingredients for commercial beverage production. The further inclusion of at least one ingredient selected from soluble fibers, bulk sweeteners, amino acids, peptides, and soluble proteins enables the resulting highly solubilized/transparent mineral complex (i.e., enhanced solubilization) to be transformed into a powder utilizing methods known in the art (including spray drying and freeze drying). The resulting dry powder, which may include excipients known in the art to maintain free-flowing powders (e.g., fumed silica), is readily added and solubilized within the traditional commercial beverage production methods. The preferred formulation includes trehalose providing a synergistic impact on both protein (and amino acids, peptides) protection against thermal degradation/denaturing and superior bone health. Trehalose, as well as other polyols, is a low glycemic sweetener thus promoting health in terms of obesity and diabetes. A preferred solubilized fiber FiberSol-2.sup.™ (ADM, Decatur, Ill., USA) is readily soluble up to 70% w/w % solids in water/juices etc.

Natural Opacifier

The inventive complex further includes embodiments that result in providing a natural source of opacity to a beverage while concurrently providing health and nutrition benefits. One preferred embodiment is comprised of the enzymatically modified caprine casein resulting in the caprine caseinophosphopeptide (CPP). The specifically high content of MCT and calcium increases the opacity of beverage formulations, as the CPP that is high in beta-casein content, has a high affinity for iron. The highly soluble complexes comprised of TruCal.sup.™ and caprine CPP formed in the presence of chitosan having embedded iron (or alternatively iron-added) preferably as a chitosan lactate derived from microbial fermentation (Cargill, USA), yield a very "milky" solution. These findings have application in the food, pharmaceutical, and cosmetic industries as an all natural "opacifiying" agent (and for whitening aqueous food compositions). Exemplary health benefits of iron-added chitosan complexed with TruCal.sup.™ include enhanced calcium, magnesium, and iron absorption for healthy and strong bones. The preferred embodiment is far superior to the prior art of calcium citrate in terms of promoting bone density and bone mechanical strength. The presence of iron is recognized in the literature as being a vital component for bone mineral density (Harris et al. in J. Nutr. 133:3598-3602 (2003)).

Transparent Beverage Preparation

For a calcium-fortified beverage (480 mg Ca/240 mL) with a serving size of 8 oz (240 mL) the amount of each ingredient would be as follows: calcium carbonate 1.2 grams (0.5% w/v), acid-soluble caprine CPP-chitosan complex: 0.96 grams (0.4% w/v), and citric acid 0.72 grams (0.3% w/v). For a calcium-fortified beverage (960 mg Ca/240 mL) with a serving size of 8 oz (240 mL) the amount of each ingredient would be as follows: calcium carbonate 2.4 grams (1.0% w/v), acid-soluble caprine CPP-chitosan complex: 1.92 grams (0.8% w/v), and citric acid 1.44 grams (0.6% w/v).

The preferred embodiment of the transparent beverage utilizes the acid-soluble CPP-chitosan complex as prepared by a two-step precipitation procedure. The two-step precipitation procedure is conducted only when using high amounts of the acid-soluble caprine CPP-chitosan complex (0.5%-1% w/v) for incorporation into carbonated transparent beverages containing calcium carbonate as the calcium source. For incorporation into highly transparent calcium fortified beverages containing calcium lactate or calcium gluconate as the calcium source, you can use the acid-soluble caprine CPP-chitosan complex prepared by the one-step precipitation procedure, but the level of the acid-soluble caprine CPP-chitosan complex cannot be higher than 0.05% (w/v).

A particularly preferred embodiment utilizes both a calcium and magnesium fortified beverage containing from about a 2:1 ratio to a 1:1 ratio of acid-soluble caprine CPP-chitosan complex precipitated with Ca and Mg respectively.

EXEMPLARY 15

Calcium-Fortified Apple Juice Containing Caprine CPP-Chitosan Complexed with TruCal.sup.™

Step 1: To 1000 ml of 100% apple juice Mott's.sup.™ with no added sugar (ingredients: apple juice, water, and apple juice concentrate) was added 0.14% (w/v) high methoxy pectin (HMP) #7050 (Cargill Food & Pharma Specialties, Cedar Rapids, Iowa, USA) (1.40 grams) followed by homogenization with a hand-held homogenizer.

Step 2: 3.33 grams of calcium gluconate (9.48% elemental calcium) and 3.83 grams of calcium lactate (13.95% elemental calcium) were added to the apple juice under constant stirring. Each 8 Oz (240 ml) of apple juice contains 75.76 mg elemental calcium from calcium gluconate and 128.23 mg elemental calcium from calcium lactate (approximately 200 mg elemental calcium per serving).

Step 3: 0.04% (w/v) caprine CPP-chitosan complexed with TruCal.sup.™ (0.40 grams) is then added to the calcium-fortified apple juice followed by homogeneous mixing.

Step 4: The calcium-fortified apple juice containing the caprine CPP-chitosan complexed with TruCal.sup.™ is transferred to a bottle and capped. Heat sterilization is conducted for 20 minutes at 83° C.

Samples of caprine CPP-chitosan "complexed" with TruCal.sup.™ were used to prepare either fruit beverages (i.e., apple juice) or transparent beverages (with added malic acid and citric acid) are as follows: Product "A" (TruCal.sup.™ with milk peptide, calcium lactate, and chitosan lactate with added iron derived from microbial fermentation (Cargill Food & Pharma Specialties, Cedar Rapids, Iowa, USA)); Product "B" (TruCal.sup.™ with milk peptide, calcium lactate, chitosan lactate with added iron derived from crab shells (Orcas International Corporation, Flanders, N.J., USA)); Product "C" (TruCal.sup.™ with milk peptide, calcium lactate, chitosan citrate derived from microbial fermentation (Cargill, USA)); and Product "D" (TruCal.sup.™ with milk peptide, calcium lactate, chitosan citrate derived from crab shells (Orcas International Corporation, USA)). Another set of calcium-enriched beverages were prepared as above but replacing calcium lactate by either calcium chloride or calcium gluconate. The taste of the calcium-enriched formulations containing calcium lactate was superior and achieved a transparent beverage w/300 mg of elemental calcium per 8 Oz serving size.

Preferred means to fully hydrate the peptides include trehalose, sucrose or corn syrup solids (i.e., glucose). This is particularly important for higher solubility or dispersability in the presence of high amounts of otherwise insoluble mineral salts as present in TruCal.sup.™. A preparation containing 13% of Daily Value for carbohydrates, based on a serving size of 240 ml, of corn syrup solids enabled 31.25% RDI of calcium per 500 ml serving size (TruCal.sup.™ contains 28% elemental Ca) to be achieved in a transparent water beverage. The addition of a high methoxy pectin (HMP #7050) (Cargill, USA) significantly reduces cloudiness. The further addition of a highly soluble mineral salt (e.g., calcium chloride) induces the salting-in effect.

500 ppm (0.5 mg/ml) of caprine CPP-chitosan complex will prevent the precipitation of 100 ppm (0.10 mg/ml) of elemental calcium (100% of calcium-solubilizing power). The bone mineralization studies detailed in the original patent application were conducted with only 0.05% (w/v) caprine caseinophosphopeptide (CPP) supplemented with calcium (300 ppm). The calcium source utilized in the study was calcium gluconate, recognized as having high solubility in water.

EXEMPLARY 16

Solubility Enhancement of TruCal.sup.™ for Beverage Applications

Product "A" (TruCal.sup.™ with milk peptide, calcium lactate, and chitosan lactate with added iron derived from microbial fermentation (Cargill, USA)); Product "B" (TruCal.sup.™ with milk peptide, calcium lactate, chitosan lactate with added iron derived from crab shells (Orcas International Corporation, USA)); Product "C" (TruCal.sup.™ with milk peptide, calcium lactate, chitosan citrate derived from microbial fermentation (Cargill, USA)); and Product "D" (TruCal.sup.™ with milk peptide, calcium lactate, chitosan citrate derived from crab shells (Orcas International Corporation, USA)).

Corn syrup solids (15% w/v), high methoxy pectin (0.35% w/v), TruCal.sup.™ milk peptide complex (0.04% w/v), citric acid (0.10% w/v), malic acid (0.35%), calcium chloride dihydrate (0.44% w/v), trehalose (2% w/v), and double deionized water (81.72% w/v). Dissolve the corn syrup solids, high methoxy pectin, citric acid, malic acid and calcium chloride dihydrate in double deionized water with the use of a hand-homogenizer for 3 minutes. The TruCal.sup.™-milk peptide complex is added to this aqueous solution followed by homogenization for another 3 minutes. 1.8 grams of TruCal.sup.™ in a 500 ml serving size will give 50% RDI of calcium. The TruCal.sup.™-milk peptide complexes (Product A, Product B, Product C, and Product D) contain on average 8 mg elemental calcium as TruCal.sup.™. The calcium chloride dihydrate provides 60% RDI of calcium in a 500 ml serving size. The total amount of elemental calcium provided by the transparent beverage is 1,108 mg. The samples are poured in a clear glass bottle and heated at 85° C. for 15 minutes. The process of pasteurization enhances the solubility of the TruCal.sup.™-milk peptide complex (enhanced transparency of the calcium-fortified beverage). These calcium-fortified beverages remain transparent at room temperature for at least 30 days.

| Product | Content | Amount in 500 ml |
|---|---|---|
| A | Product A plus TruCal.sup.TM | 0.20 g plus 1.80 g |
| B | Product B plus TruCal.sup.TM | 0.20 g plus 1.80 g |
| C | Product C plus TruCal.sup.TM | 0.20 g plus 1.80 g |
| D | Product D plus TruCal.sup.TM | 0.20 g plus 1.80 g |
| E | TruCal.sup.TM | 1.8 g |

In all above samples tested chalkiness, cloudiness, and sedimentation are not observed, and the acidic taste is acceptable for beverage formulation.

During the development of the antioxidant and transparent beverage applications, it became readily apparent that the inventive complexation approach was a foundation for flavor platforms. The specific benefits, realized as a result of controlling ingredients (i.e., mineral salts, acids, enzymatically modified proteins, chitosan, etc.) and process steps resulted in powders having sweetness, creaminess, controlled saltiness, and reduced bitterness.

Low Sodium Salt Replacement

An embodiment of the complex has been created with the combination of TruCal.sup.™ "complexed" with caprine CPP-chitosan, whereby the chitosan is a lactate salt with added iron. The chitosan (manufactured by Cargill) has a very good taste profile due to the bitterness being almost entirely masked by TruCal.sup.™ and the chitosan lactate. The normal chalkiness associated with calcium mineral salts is no longer perceived. The degree of saltiness is controlled by both the amount of salted-in mineral salts and the pH level. As noted earlier in the sequential salting-in process, a preferred embodiment contains a level of sodium reduced by at least 50% by the final mineral salting-in being NaCl. Numerous food applications are such that the perception of salt is a surface phenomenon, thus a presence of NaCl towards the periphery of the salted-in peptide will represent a higher perceived level vs. either stand alone NaCl crystals or salted-in peptides comprised entirely of NaCl. Furthermore, the caprine CPP effectively binds cations and keep them soluble in the digestive tract yielding higher bioavailability for the less inherently soluble minerals including iron.

Peptide and Hydrolysate Debittering

The preparation of the preferred peptide as complexed with a chitosan salt (preferably with chitosan lactate) has resulted in debittered peptides (anticipated for amino acids and protein hydrolysates as well). The combination further protects the peptide against degradation thus enhancing and prolonging the mineral transport capabilities leading to superior bioavailability of a wide range of minerals. Virtually any protein (e.g., soy, canola, pea, etc.) is a candidate for enzymatic modification by protease (e.g., trypsin) to split the protein molecule into small protein peptides. The preferred chitosan salt is chitosan lactate to bring the pH down to 3.0-4.0, resulting in a peptide having very low bitterness and saltiness. The key to mask the bitterness of caprine CPP is to neutralize the caprine CPP-chitosan preparation with an alkali (to a range of pH 5.5-6.5, though the preferred embodiment has a pH 6.0).

Mental Health

The individual benefits associated with Omega-3 rich oils and phospholipids including phosphatidylcholine, phosphatidylserine, and glycerolphosphocholine are widely recognized in the broad area of mental health. However, significant benefits are achieved beyond their individual benefits due to the high bioavailability of nutraceutical and pharmaceutical actives contained within an oil-in-water emulsion. The preferred combined formulation utilizes an Omega-3 rich oil as a carrier oil for said nutraceutical and pharmaceutical actives. Exemplary nutraceutical actives include plant sterols, vitamins (e.g., Vitamin A, D, and K), and coenzyme Q10. Preferred pharmaceutical actives are selected from the group consisting of fat soluble actives, peptides, DNA, and enzymes.

The preferred embodiment utilizes a low concentration of GPC 85 (0.01%-0.04% wt., based on the weight of the emulsion, respectively) in combination with the caprine CPP-chitosan complex (0.04% wt., based on the weight of the emulsion) in the aqueous phase. The chitosan assumes a polycationic character at acidic pH, therefore maximum interaction between the negatively charged GPC 85 and CPP-chitosan complex is observed at acidic pH. At pH 6.0, the caprine CPP-chitosan complex exhibits less positive charge (interaction with GPC 85 is at a minimum), yet still a net positive charge.

Another embodiment is further comprised of DNA. The caprine CPP-chitosan complex exhibit a strong net positive charge (and caprine CPP contains high amounts of a basic amino acid:lysine). Caprine CPP also contains high amounts of beta-casein. The ideal pH for chitosan (and milk proteins or peptides) to bind to DNA is around 6.0-6.5. A more preferred embodiment further includes the presence of an "electron donor transfer" likely to further enhance the bioavailability of DNA for gene therapy and other nucleotides (i.e., pyrimidines such as citodine or uridine). A more specifically preferred embodiment further includes ribose, which is a sugar present in the DNA molecule and other nucleotides. A complex of ribose, caprine CPP-chitosan, gamma-cyclodextrin (CAVAMAX CoQ10.sup.™), and polyphenols have the ability to stabilize Omega-3 rich oils in vitro, with the significant in vivo benefits attributed to the synergistic impact of the combined formulation. The Maillard Reaction Products (MRPs) formed due to interaction of the free amino group of the amino acid lysine present in the caprine CPP molecule and the free amine group of D-glucosamine present in the chitosan molecule and a reducing sugar (glucose units present in Cavamax CoQ10.sup.™) exhibit "antioxidant" activity. The preferred embodiment is anticipated to provide protection to the range of nucleosides, nucleotides, proteins, protein hydrolysates, peptides, amino acids, and enzymes.

The preferred embodiment inherently incorporates chitosan's recognized properties as noted in U.S. Pat. No. 6,184,037 by Rolland, et al. on Feb. 6, 2001 titled "Chitosan related compositions and methods for delivery of nucleic acids and oligonucleotides into a cell" being useful in complexing and condensing nucleic acids or complexing oligonucletides. DNA, which is a polyanionic nucleic acid has a high net negative charge due to the presence of two phosphate moieties on each base pair. Rolland further teaches the conclusion that "DNA is an excellent candidate for complexation with chitosan and chitosan oligomers for non-viral gene delivery". Neutralization of the negative charge of DNA by the amine groups of chitosan and chitosan oligomers results in condensation of DNA into a compact particle which protects the DNA from nuclease degradation and delivers the DNA, either specifically or non-specifically, to target cells". Rolland does not anticipate the benefits of incorporating Omega-3 rich oils as a further means of increasing the efficacy and bioavailability associated with the preferred embodiment.

Yet another embodiment includes a range of individual actives recognized for immune system enhancement. One such active is beta-glucan being recognized as having an immunomodulatory action. The beta-glucan has multiple negatives associated with the stand-alone active, which include non-desirable taste, low solubility, and low bioavailability. A preferred chitosan-beta-glucan complex has reduced bitterness, high bioadhesion, and higher solubility, all of which contribute to superior bioavailability. The more preferred complex is further comprised of caprine caseinophosphopeptides (CPP). And the particularly preferred complex has zinc lactate salted-in as a means of providing high bioavailability of zinc (also recognized for immune system enhancement). The selection of caprine caseinophosphopeptides (CPP) further enhances the bioavailability of magnesium. Another preferred modified caprine CPP-chitosan is a further complex of caprine caseinophosphopeptide, chitosan and beta-glucan. The resulting complex, without being bound by theory, is an especially powerful immunity enhancer as the combined complex performs better than each individual component due to the synergistic effects of high zinc binding, the bioadhesive and protein protection by the chitosan, the higher chelation capabilities as compared to animal chitosan by the combined chitosan and beta-glucan, and superior electron transfer due to the iron presence in the chitosan creating an iron-sulfur cluster due to the complex of caprine caseinophosphopeptide and chitosan. The specifically preferred caprine caseinophosphopeptide-zinc-beta-glucan-chitosan is further combined with EDTA as a further means to prevent the "leakage" under high acidic pH (i.e., ≦4.0) of ferrous ions 'bound' to the chitosan salt leading to catalytic oxidation of lipids. Another benefit of the synergistic combination is the reduced bitterness of the zinc and beta-glucan making the product more suitable for functional food and beverage products. Zinc and magnesium are especially noted for their direct effect on osteoblastic activity. Another preferred delivery includes the further addition of omega-3 oils as a means to inhibit inflammation. A more preferred delivery further includes Vitamin D within the Omega-3 to provide high efficacy delivery of Vitamin D (and/or additional fat soluble Vitamins, nutraceuticals, and pharmaceuticals). The further inclusion of a thermally-stabilized lactoferrin, as provided by TAMUS 1408 has both an "in-food" and "in-vivo" impact, which are reduced lipid oxidation and enhanced immunity, respectively.

Numerous observations of magnesium have been cited by Guosong Liu in "Magnesium for Memory" Prepared Foods Newsletter Dec. 6, 2004. Liu further states that magnesium in the American diet has declined since the Industrial Revolution and that the high fat content of the modern diet prevents magnesium from being absorbed. In his experiment, he fed lab rats the equivalent of a human dose of 400 mg of magnesium a day. The result, he said, was that the mineral increased the activity of receptors that control learning and memory.

Specifically, it enhanced the activity at the synapse, the gap between two neurons, or brain cells. However, numerous other factors not cited by Liu adversely impact magnesium bioavailability. These include competitive interaction with calcium salts. Therefore the preferred embodiment of caprine caseinophosphopeptides (CPP) further enhances the bioavailability of magnesium ions in part due to the high medium-chain-triglycerides (MCT) content. The particularly preferred embodiment comprises salted-in magnesium lactate. Certain foods, due to the high acidity taste of lactate salts, can utilize potassium hydroxide to neutralize the lactic acid present in the chitosan preparation (i.e., lactate) during the preparation of caprine CPP. Magnesium hydroxide and calcium hydroxide can also be utilized in combination of instead of potassium hydroxide as a means to reduce the peptide "bitterness". The preferred method being a sequential salting-in process of lactic acid salts followed by the hydroxide salts. In addition to the mental health gains associated with magnesium, numerous additional benefits including energy metabolism and protein synthesis are recognized.

The combination of phospholipids with chitosan has multiple synergistic impact including permeation enhancers. A preferred embodiment includes phosphatidylserine (PS), which is an acidic phospholipid that in combination phosphatidylcholine (PC), significantly decreases the iron-induced oxidation of egg yolk PC when utilized as an emulsifier in Omega-3 rich oils. Phospholipids 'rich' in PC are utilized to increase "bilayer" adhesion whereby the increased bilayer adhesion between the "negatively" charged phospholipids PC and "positively" charged caprine CPP-chitosan complex to stop Omega-3 degradation in O/W emulsions. Phospholipids 'rich' in phosphatidylserine (PS) (i.e., SerineAid 50P.sup.™) are necessary to chelate iron present in the egg yolk phospholipids, in particular in acidic emulsions (pH<5.0). Oil-in-water emulsions prepared with egg yolk PC (Omega 6-PL-85.sup.™) and alpha-glyceryl phosphoryl choline (GPC 85.sup.™) exhibit enhanced oxidative stability because GPC 85.sup.™ is also an effective iron chelator. Clearly the preferred embodiment introduces synergistic benefits when at least one emulsifier is selected from the group of phospholipids consisting of PC, PS (i.e., SerineAid 50P.sup.™) and alpha-glyceryl phosphoryl choline (GPC 85.sup.™). GPC 85.sup.™ is particularly preferred when complexed with either the caprine CPP-chitosan complex and/or caprine CP alone. Formulations that require additional phospholipids beyond the required levels for complexation preferably are comprised of GPC 85.sup.™ within the water phase of the emulsion.

Literature supports that mucoadhesive polymers enhance the peroral peptide drug delivery. Thiolated polycarbophil and thiolated chitosan in combination with reduced glutathione (GSH) are potent enhancers of peptide transport across intestinal mucosae by increasing the parecellular permeability due to opening of intercellular junctions (Bernkop-Schnürch et al. in J. Control Release 93, 95-103 (2003)). Furthermore calcium plays an important role in maintaining the thermodynamic stability of several serine proteases (e.g., trypsin), which is the basis of their resistance against autoproteolysis. Additionally, chitosan improves transport by increasing the paracellular permeability of the intestinal epithelium (Sharma et al. in Pharmazie 61, 495-504 (2006)). Mucoadhesive polymers as platforms for peroral peptide delivery comprised of chitosan-EDTA conjugates are very useful drug-carrier matrixes in overcoming the enzymatic barrier to orally administered peptide and protein drugs (Bernkop-Schnürch, A. and Pasta, M. in J. Pharmaceutical Sciences 87, 430-434, 1998). The preferred embodiment comprised of both caprine CPP-chitosan and EDTA, though the EDTA is contained within the water phase as a means of protecting the Omega-3 oil, is anticipated to have comparable performance to the chitosan-EDTA conjugates.

Muranishi et al. in Chem Phys Lipids 28: 269-279 (1981) further supports that fatty acids including oleic, capric, and linoleic acids have a strong and rapid action on permeability of lipid bilayer, while chelating agents such as EDTA, citric acid, phytic acid have strong to moderate activity. Thus it is reasonable, without being bound by theory that the preferred caprine CPP-chitosan complex combined with the preferred presence of capric MCT, oleic fatty acids, EDTA, chitosan, and oils rich in phytic acid would further improve the permeability. And the superior binding of calcium, magnesium, and zinc to the preferred caprine caseinophosphopeptide (CPP) further enhances the bioavailability of said minerals.

A yet further embodiment of the invention is the "encapsulation" of the Omega-3 rich oil in olive oil. The combination of olive oil, which is rich in ferulic acid, and lactoferrin is a synergistic antioxidant combination to protect Omega-3 rich oils from oxidation. Clark et al. as cited in http://www.algatech.com/bio.htm compared lycopene and astaxanthin absorption from corn oil and olive oil emulsions in rats. Absorption of lycopene and astaxanthin from both oils increased with the amount infused into the rat's duodenum. The average recovery of astaxanthin in the lymph from the olive oil emulsion was 20%, but decreased to 13% from emulsions containing corn oil. Lycopene was not as well absorbed as astaxanthin. The average recovery of LYC was 6% from olive oil emulsions but only 2.5% when infused with corn oil. They concluded that the type of oil with which a carotenoid is consumed can substantially influence its absorption. Astaxanthin is a powerful antioxidant and can serve as a potent free-radical scavenger. Moreover, astaxanthin has been found to provide many essential biological functions, including protection against lipid-membrane peroxidation of essential polyunsaturated fatty acids and proteins, DNA damage and UV light effects; it also plays an important role in immunological defense. Astaxanthin is capable of crossing the blood-brain barrier in mammals. The preferred embodiment of Omega-3 rich oil, which is an orthomolecule, encapsulated by olive oil, which is rich in ferulic acid, in combination with thermally-stabilized lactoferrin, green tea extracts (or gallic acid) and coenzyme Q10 encapsulated by gamma-cyclodextrin all within micelles comprised of at least one of the group consisting of chitosan, caprine CPP-chitosan, caprine CPP, GPC 85.sup.™, Omega 6-PL-85.sup.™, and SerineAid 50P.sup.™ has superior bioavailability and free radical protection both in vitro and in vivo.

Another embodiment further includes trehalose. Trehalose is recognized as a means to protect proteins from unfolding, thus it is obvious that trehalose will protect the caprine caseinophosphopeptide (CPP) of the present invention. Trehalose has also been identified as being effective against protein agglomeration in mice having the Huntington protein. Without being bound by theory, the further inclusion of trehalose providing superior oxidation protection to Omega-3 rich oils (i.e., by encapsulating the Omega-3 rich oil during the process of spray drying) has the further potential to enhance mental health by the synergistic combination of Omega-3 and trehalose. It is recognized that the biosynthesis of trehalose phosphate can occur by either one of two reactions: UDP-glucose+glucose-6-P>>trehalose-P+UDP. It is further hypothesized that in vivo trehalose has a role within mental health in the production of uridine, citodine, and/or choline within the brain. Thus the particularly preferred embodiment is comprised of a trehalose to Omega-3 ratio ranging from a low of 5% w/w of water phase, 5% w/w of total oil phase in emulsion to a 1:1 ratio of trehalose to Omega-3 fraction of Omega-3 rich oil.

Electron Transfer

Without being bound by theory, the creation of iron sulfur clusters is a fundamental component in the electron transfer from the oil phase into the water phase of the emulsion. Thus, effectively an electron transfer bridge is created across the interface of between the oil and water phase. The existence of this electron transport bridge is critical to the realization of significantly superior oxidative stability of lipids. The irony of this result is such that, iron which is otherwise a procatalyst, must be present in at least trace amounts as a means of creating the electron transfer bridge. Such electron transport bridge includes thialoto-bridged complexes. Electron-rich thiolato groups have a great affinity for various metal ions. This includes metal-bound thiolato sulfur centers. Broadly, the incorporation of thiolated complexes, metalloproteins and/or protein complex having an iron-sulfur cluster within the emulsion interface, without being bound by theory, enhances electron transfer between the phases.

The further inclusion of an electron transfer mediator within the antioxidant and nanoemulsion compositions, without being bound by theory, enhances electron transfer out of the lipid phase of the emulsion into the water phase. The preferred electron transfer mediator is potassium hydroxide, an acceptable food ingredient. The potassium hydroxide serves a significant secondary role of providing potassium mineral supplementation, a noted deficient mineral especially in the American diet.

Without being bound by theory, the inventive combination of an electron transfer mediator, a molecular electron transfer bridge, and an iron-sulfur cluster (or metalloproteins) creates an aqueous, room temperature electride solution as indicated by the presence of a sapphire blue solution indicative of free electrons (increased free electron flow). A wide range of applications are anticipated for stable room temperature electride solutions, including nutraceutical, pharmaceutical, energy transfer, and oxidative stability applications.

U.S. Pat. No. 7,045,339 by Sorenson, Jr., et al. on May 16, 2006 titled "Electron donors for chlorinated solvent source area bioremediation" notes that lactic acid or salts of lactic acid, or mixtures thereof are illustrative electron donors including oleyl lactylic acid, linoleyl lactylic acid, linolenoyl lacylic acid, stearoyl lactylic acid, palmitoyl lactylic acid, myristoyl lactylic acid, lauroyl lactylic acid, caproyl lactylic acid, mixtures thereof, mixtures with fatty acids or salts thereof, mixtures with lactic acid or salts thereof, mixtures with fatty acids and lactic acid and salts thereof, and the like. In a specific embodiment of the invention, the electron donor is a member selected from the group consisting of lactic acid, salts thereof, lactate esters, and mixtures thereof. Illustrative salts of lactic acid include sodium lactate, potassium lactate, lithium lactate, ammonium lactate, calcium lactate, magnesium lactate, manganese lactate, zinc lactate, ferrous lactate, aluminum lactate, and mixtures thereof, wherein sodium lactate is especially illustrative. In another specific embodiment of the invention, the electron donor is a member selected from the group consisting of oleyl lactylic acid, oleic acid or salts thereof, and lactic acid or salts thereof. The preferred embodiment of the present invention for chitosan is a chitosan lactate. A more preferred embodiment includes lactate salts selected from the group of potassium, calcium, zinc, and magnesium due to their multifunctional role within the applied food, nutraceutical or pharmaceutical system. Potassium is a superior electrolyte as compared to sodium. Zinc and magnesium play vital health roles in bone, mental, and immune system health. Caprine CPP-chitosan complexes comprised of zinc lactate demonstrated superior antioxidant performance to the other lactate salts.

Without being bound to theory, electron transfer reactions (most notably within oil and water emulsions) depend upon multiple factors such as electrolyte concentration (potassium is the mineral activator within cells), lipids (phosphatidylcholine and phosphatidylserine), divalent cations (calcium, magnesium), and iron-sulfur clusters (chitosan lactate with added iron; caprine CPP contains cysteine). The specific protection of Omega-3 oils within oil-in-water or water-in-oil emulsions is highly dependent on electron transfer across the micelle interface. A more preferred embodiment further includes whey protein (concentrates and isolates) that are rich in cysteine. Cysteine, which is recognized as a means to maintain a healthy immune system through glutathione synthesis yields glutathione, a potent antioxidant within in vivo cellular structures. The particularly preferred embodiment of the caprine CPP-chitosan complex has sufficient iron within the matrix to create an iron-sulfur cluster. Cysteine is a sulfur-containing amino acid, which is most likely the critical amino acid in creating the iron-sulfur cluster. Therefore, the superior protection against lipid oxidation mimics the in vivo cellular structure that is an interface layer comprised of phospholipids, channel proteins, and catalytic proteins. The inventive caprine CPP-chitosan complex (in the preferred embodiment) plays the role of the channel protein by enabling efficient electron transport across the oil-water interface. The further inclusion of a lactic protein furthers the electron transport mechanism, as lactic acid is an electron donor. The further inclusion of lactoferrin mimics a catalytic protein. The preferred protein is whey protein with lactic acid. The particularly preferred protein is a whey protein hydrolysate isolate with lactic acid. And the further inclusion of coenzyme Q10 encapsulated by gamma-cyclodextrin provides for the production of Maillard Reaction Products with antioxidant properties through the glucose present in gamma-cyclodextrin during food processing (i.e., pasteurization, baking). Without being bound by theory, the mechanisms taking place are as follows: (1) Plant-derived polyphenols are metal-chelating agents and free-radical scavenging agents; (2) Coenzyme Q10 regenerates tocopheryl free radicals (prooxidant activity) into antioxidative tocopherol molecules (antioxidant activity); (3) Gamma-cyclodextrin (CAVAMAX.sup.™) is comprised of glucose which enables the formation of thermally-derived compounds known as Maillard Reaction Products with specific antioxidant activity; (4) Tocopherols and tocotrienols are highly effective antioxidants in oil-in-water and water-in-oil emulsions at levels greater than 500 ppm; (5) Potassium hydroxide, which is the preferred electron transfer mediator, is used to adjust the pH of the oil-in-water or water-in-oil emulsions to 6.0, and to inject electrons to chemical structures containing an aromatic ring (i.e., tocopherols, tocotrienols, grape seed extract, grape pomace extract, bee propolis, green tea, coenzyme Q10, BHA, BHT, and TBHQ.

Modulation of Metabolic Pathways by Influencing Electron Flux

The utilization of N-acetyl cysteine, which is a well-known scavenger of reactive oxygen species (ROS) is anticipated as a means of facilitating electron transport in addition to the recognized role of protecting the liver from injury. The liver is the organ that detoxifies our body from harmful substances such as alcohol, nitrates present in cured meats, pesticides present in conventional grown fruits and vegetables, etc. The U.S. patent application by McCleary "Metabolic Uncoupling Therapy" (20040043013) focuses on the importance of electron transport reactions within the human cell though fails to recognize the importance of in vitro protection of Omega-3 rich oils in order to provide oxidative stability. The preferred embodiment of the present invention is superior and substantially novel by the realization of 1) coenzyme Q10 being encapsulated by cyclodextrin, preferably gamma-cyclodextrin, 2) encapsulated coenzyme Q10 being within the oil phase, 3) same but for alpha lipoic acid as in #2 and #1, 4) the presence of amino acids in the form of a complex having an iron-sulfur cluster, and 5) The U.S. Pat. No. 6,579,866 by McCleary on Jun. 17, 2003 titled "Composition and method for modulating nutrient partitioning" though explicitly requires the utilization of hydroxycitric acid, whereas the inventive preferred embodiment recognizes the significant detriment of citric acid to the emulsion and oxidative stability of the Omega-3 rich oils.

Additional antioxidants including eugenol, which is recognized as enhancing the metabolism of DHA and inactivating free radicals, grape seed extract, and ginger, turmeric, spirulina, and green tea which are known to contain Superoxide Dismutase "SOD" (a potent in vivo natural antioxidant). A particularly preferred antioxidant is or contains gallic acid, such as green tea. In the present invention gallic acid is also used as a buffering agent at concentrations ≦50 ppm (0.0005 wt. %) to adjust the pH of the oil-in-water emulsions to 6.0 in combination with the preferred electron transfer mediator potassium hydroxide. Gallic acid is an antibrowning agent and a potent antioxidant. Gallic acid scavenges superoxide anions that are generated enzymatically. The oxidation of unsaturated fatty acids in biological membranes decreases membrane fluidity and disrupts membrane structure and function (Machlin, L. and Benedic, A. in FASEB J. 1, 441-445 (1987); Slater, T. F. and Cheeseman, K. H. in Proceedings of the Nutrition Society 46, 1-12 (1987). Cellular damage due to lipid peroxidation causes serious disturbance that can result in ischemia-reperfusion injury (Sugawara et al. in J. Clin. Exp. Med. 163, 237-238 (1992)), coronary arteriosclerosis (Kok et al. in Atherosclerosis 86, 85-90 (1991)), or diabetes mellitus (Sugawara et al. in J. Clin. Exp. Med. 163, 237-238 (1992); it also is linked to aging and carcinogenesis (Yagi, K. in Antioxidants and Disease Prevention; CRC Press: Boca Raton, Fla., USA (1997); Garewal, H. S. in Antioxidants and Disease Prevention; CRC Press: Boca Raton, Fla., USA (1997)). Inhibition of membrane peroxidation has a protective effect on the initiation and promotion of certain cancers. In general, various reactive oxygen molecules link damage to the initiation and development of cancer. The primary role of antioxidants is to protect against such damage. Therefore, gallic acid or green tea, which is a rich source of gallic acid, can be considered even as cancer-fighting ingredients or chemopreventive agents. A research report by Sakagami et al. in Anticancer Res. 17, 377-380 (1997) indicates that gallic acid induced apoptotic cell death in human promyelocytic leukemia HL-60 cells. Because superoxide anions reportedly enhanced the oxidation rate of L-tyrosine to L-DOPA by tyrosinase (Wood et al. in Biochem. Biophys. Acta 1074, 378-385 (1991)), the scavenging activity of gallic acid and green tea is of considerable benefit.

A surprising feature of the bioactive complex of the present invention is the creation of a sapphire blue color within an aqueous solution. It is hypothesized that the sapphire blue color, which without being bound by theory, is indicative of free electrons such as electrides. The blue color only is evident in caprine CPP-chitosan formulations containing chitosan lactate with embedded iron. The blue "solution" is obtained with chitosan lactate manufactured by Pronova Biopolymer Corporation (Portsmouth, N.H., USA) and caprinecaseinophosphopeptide (CPP) at about 400 ppm (caprine CPP-chitosan complex), in combination with gallic acid at about 20 ppm. Increasing the levels of gallic acid increased the deepness of the blue color. The pH of the solution is at least 6.0 (can also be greater, but not less). This finding is particularly unique in that electrides to date have not been present at either room temperature or in the presence of water (let alone within an aqueous solution). Applications of such an electride solution range from energy conversion applications to energy transfer (e.g., fuel cells, solar to electricity conversion, heat transfer, etc.).

The preferred caprine CPP preparation contains cysteine (bovine CPP does not contain cysteine, another reason for enhanced effectiveness of the caprine CPP-chitosan complex vs. a bovine CPP-chitosan complex). The —SH groups of L-cysteine decide the conformation of proteins (and derived peptides) and the catalytic activity of enzymes. Without being bound by theory, the thiol (—SH) groups of cysteine forms "iron-sulfur centers" (iron atoms paired with an equal number of acid-labile sulfur atoms) that are essential for electron transfer. Recent experimental studies have provided evidence that the —SH groups of L-cysteine enhance the electron transfer ability between protein molecules and chitosan-stabilized gold nanoparticles (Feng et al. in Anal. Biochem. 342, 280-286 (2005)). These active —SH groups (i.e., L-cysteine) of proteins (and peptides) have also been shown to facilitate electron transfer and electrocatalyze the redox of phenolic compounds when dissolved in aqueous solution (Zhao et al. in J. Environmental Science and Health 41, 447-456 (2006)). The "high" affinity of the beta-casein component present in high amounts in caprine CPP (>50%) for iron as compared with bovine CPP (<30%) is one major factor proving the efficient electron transfer turnover-rate of the caprine CPP-chitosan complex. Thus, the caprine CPP molecule "strongly" interacts with the iron "embedded" in the chitosan molecule. In the event that the source of chitosan is naturally (or due to production processes) iron deficient, the chitosan can be embedded with iron during the creation of the chitosan complex. Chitosan complexes have ranged with 20 ppm of iron to 700 ppm. In the event that the chitosan complex is being utilized to provide antioxidant protection for an "encapsulated" oil/lipid, it is essential to maintain the caprine CPP-chitosan with the embedded iron to be less than 500 ppm of the total emulsion weight. It is anticipated that both additional levels of chitosan and/or caprine CPP-chitosan can be utilized only when said chitosan is void of iron, especially under high acid pH conditions. Under high acid conditions, the embedded iron is "leaked" from the matrix and becomes the recognized pro-catalyst. Thus one of the novel features of the preferred embodiment is the superior antioxidant performance during the presence of an otherwise traditional pro-oxidant.

In living organisms, iron-sulfur centers (clusters) are associated with an enzyme, succinate NADH dehydrogenase, which is involved in electron transport reactions. By undergoing Fe (II)-Fe (III) cycles, the prostetic groups of this succinate NADH dehydrogenase transfer reducing equivalents to the next electron carrier ubiquinone (coenzyme Q). The complex of succinate NADH dehydrogenase with the iron-sulfur proteins contains two kinds of electron-carrying structures. Real life is emulated in a preferred embodiment containing the caprine CPP-chitosan complex of the present invention. The caprine CPP molecule 'per se' is a 'bioactive' milk protein fraction or peptide whereas an enzyme is a protein specialized to catalyze a specific metabolic reaction.

This in vivo process is emulated in vitro in a test tube that contains an aqueous solution of caprine CPP-chitosan complex (0.05% w/v) where the iron-sulfur centers (clusters) are associated with a casein protein (or preferably a casein peptide, or particularly preferred a caprine CPP), and the chitosan molecule having iron present. By undergoing Fe (II)-Fe (III) cycles, the caprine CPP-chitosan complex (iron-sulfur complex) acts as an electron carrier structure transporting electrons to or from ubiquinone (coenzyme Q10). Electron transfer reactions between the iron-sulfur clusters of the CPP-chitosan complex and coenzyme Q10 play an important role in stabilizing Omega-3 oils against oxidative degradation in vitro and very likely in vivo (the living cell).

Moreover, iron (II) complexes might be formed with the further inclusion of gallic acid (Fenton-type reactions) (Strlic et al. in J. Agric. Food Chem. 50, 6313-6317 (2002)). Gallic acid is known to be readily oxidized, chemically or electronically, in acidic and alkaline solutions. The o-quinone products from gallic acid are formed via the semiquinone radical and are susceptible to secondary reactions at pH>7. It should be noted here that we have conducted our electron-transfer studies at pH 6.0; therefore, gallic acid does not fully oxidize. Furthermore, studies conducted by other scientists have shown that at pH<7.0 iron (II) does not complex with gallic acid. Our studies by gas chromatography (GC) with O/W Menhaden oil-based emulsions emulsified with egg yolk PC (Omega 6-PL-85.sup.™) confirm research by Strlic et al. (2002) in which the addition of Fe (II) or Fe (III) to an aqueous solution of gallic acid has a prooxidative effect. Therefore, the main mechanism taking place in our studies conducted with caprine CPP-chitosan complex (500 ppm), gallic acid (10 ppm-50 ppm), and coenzyme Q10 (0.25%-1.0%) is due to electron transport reactions between the CPP-chitosan complex (iron-sulfur complex) and coenzyme Q10. Indeed, control samples containing gallic acid, alone or in combination with coenzyme Q10, exhibit prooxidative properties, and it promotes the production of hydroxyl radicals due to the presence of iron from egg yolk PC (Omega 6-PL-85.sup.™). The further inclusion of trehalose at concentrations of 1% to 2% (w/v) is essential to stabilize the CPP-chitosan complex at incubation temperatures $\geq$40° C. Gallic acid is used in our studies as a "buffer" to acidify the aqueous media; subsequent addition of the preferred electron transfer mediator (0.1 N KOH) is preferred to bring pH of the aqueous solution to 6.0.

It is recognized in the art, that thionins is a family of peptides found solely in higher plants. Specifically as cited in "Biochemical fuel cells" by Eugenii Katz et.al., of Institute of Chemistry and The Farkas Center for Light-Induced Processes, The Hebrew University of Jerusalem in Jerusalem, Israel, thionin consists of 45-48 amino acid residues. 6-8 of these are cysteine forming 3-4 disulfide bonds. Microbial cells have also been grown in the presence of various nutritional substrates. For example, *Proteus vulgaris* bacteria were grown using glucose, galactose, maltose, trehalose and sucrose as primary electron donors and used in a biofuel cell with thionine as a diffusional electron transfer mediator. We, the applicants of this invention, note that the toxicity of thionin precludes the use for food ingredient applications, though the potential for both non-edible and pharmaceutical applications remains as a means to achieve excellent electron transport. Additional means to achieve electron transport reactions include ferredoxin and flavodoxin. As expected, electron transport reactions are only favored in the aqueous phase rather than in the oil phase. The higher the oil content of the emulsion ($\geq$30%), the lower the conductivity of electrons. This means relatively "poor" oxidative stability protection of Omega-3 oils when the caprine CPP-chitosan complex of the present invention is contained within the oil phase.

Electron transfer plays a vital role in numerous applications including the performance of antimicrobials. The inventive caprine CPP-chitosan complex potentiates antimicrobials, antivirals, etc. known in the art and/or serves as a primary antimicrobials or antivirals.

Although only exemplary embodiments of the invention are specifically described above, it will be appreciated that modifications and variations of these examples are possible without departing from the spirit and intended scope of the invention.

What is claimed is:

1. A bioactive composition comprising a protein fragment complex whereby the protein fragment complex is operable as an electron transfer bridge, and the electron transfer bridge is across the interface of an oil and water emulsion, wherein the electron transfer bridge contains between about 50 to 400 ppm of iron and the electron transfer bridge is an iron-sulfur cluster.

2. The bioactive composition according to claim 1, whereby the oil and water emulsion includes a water phase and an oil phase is comprised of at least one selected from the group consisting of reducing sugar including glucose, cyclodextrin, or combinations thereof, fat soluble vitamins, Omega-3 rich oils, fat-soluble nutraceutical or pharmaceutical actives, oils rich in ferulic acid including olive, rice bran, corn, or oat oils, ionic liquids, ionic emulsifiers, monoglycerides, diglycerides, or combinations thereof.

3. The bioactive composition according to claim 2, whereby the oil phase is further comprised of chelating agents including EDTA, lactoferrin, phytic acid, cyclodextrin, permeation enhancers, or combinations thereof.

4. The bioactive composition according to claim 3, whereby the oil to cyclodextrin ratio is at least 10:1.

5. The bioactive composition according to claim 3, whereby the lactoferrin is further processed by at least one means selected from the group consisting of thermally stabilizing the lactoferrin, blending with oils rich in ferulic acid, complexing with phytic acid, removing iron III from lactoferrin, complexing with EDTA, or combinations thereof.

6. The bioactive composition according to claim 2, whereby the water phase is comprised of at least one selected from the group consisting of lactoferrin, phytic acid, trehalose, acetyl L-carnitine, permeation enhancers, or combinations thereof.

7. The bioactive composition according to claim 6, whereby the trehalose to omega-3 oil ratio ranges from the lesser of 5% w/w of water phase or 5% w/w of Omega-3 phase to a 1:1 ratio.

8. The bioactive composition according to claim 2, whereby the cyclodextrin is complexed with at least one selected from group consisting of fat-soluble antioxidants, vitamins, electron donors, or combinations thereof.

9. The bioactive composition according to claim 2, whereby the composition is void of fructose, fructose syrups, and fructose derivatives.

10. The bioactive composition according to claim 2, whereby the composition is comprised of iron and the pH is less than 6.0 and whereby the composition is void of ascorbic acid or ascorbic acid derivatives.

11. The bioactive composition according to claim 2, whereby the composition is further comprised of electron transfer mediators including potassium salts, lactic acid salts, derivatives of potassium salts, derivatives of lactic acid salts, and combinations thereof.

12. The bioactive composition according to claim 2, whereby the water phase is comprised of the combination of glycerolphosphocholine and a polycationic complex.

13. The bioactive composition according to claim 1, whereby the electron transfer bridge further comprises thialoto-bridged complexes, thiolated complexes, metalloproteins, trehalose complexes, or combinations thereof.

14. The bioactive composition according to claim 1, whereby the electron transfer bridge pH is adjusted to a pH between 5.5 and 6.5 by means including potassium hydroxide, calcium hydroxide, magnesium hydroxide, or combinations thereof.

15. The bioactive composition according to claim 1, whereby the complex is further comprised of at least one selected from the group consisting of electron donor transfer, nucleotides including pyrimidines, nucleosides, ribose, cyclodextrin, antioxidants, Omega-3 rich oils, beta-glucan, or combinations thereof.

16. The bioactive composition according to claim 1, whereby the electron transfer bridge is comprised of at least one selected from the group consisting of canola protein isolate, canola protein fragment, keratin, keratin, or combinations thereof complexed with chitosan, caseinosphospopeptide complex comprising the iron-sulfur cluster.

17. The bioactive composition according to claim 1, whereby the electron transfer bridge is comprised of a pH adjuster to adjust pH between the 5.5 and 6.5 including at least one selected from the group consisting of calcium, potassium, magnesium hydroxide, dairy mineral complex, or combinations thereof.

18. The bioactive composition according to claim 1, whereby the electron transfer bridge is a chitosan complex including chitosan lactate, chitosan alpha lipoic acid, thiolated chitosan, or combinations thereof.

19. The bioactive composition according to claim 18, whereby the chitosan is comprised of iron between 50 and 400 ppm.

20. The bioactive composition according to claim 1, whereby the electron transfer bridge is further comprised of a polycationic chitosan void of iron.

21. The bioactive composition according to claim 1, whereby the composition is further comprised of egg yolk phospholipids, phospholipids with a phosphatidylcholine content greater than 40%, glycerolphosphocoline, choline, betaine, pyrimidines, nucleotides, nucleosides, trehalose, or combinations thereof.

22. The bioactive composition according to claim 1, whereby the composition is further comprised of antioxidants including vanillin, vanillin derivatives, bee propolis, grape seed extract, grape pomace extract, quercitin, tetrahydrocurcuminoids CG, ginger, turmeric, capsaicin, spirulina, tocopherol, tocopherol derivatives, tocotrienols, tocotrienol derivatives, green tea, clove, clove extracts including eugenol, walnut extracts and rosemary extracts, and rosemary extracts including carnosic acid and carnosic derivatives.

23. The bioactive composition according to claim 1, whereby the composition is an efficacious means for hypercholesterolemia prevention products, bone mineral loss prevention products, enhancing cognitive performance, reducing disorders of mental health, reducing triglyceride levels, reducing blood pressure levels, reducing arterial plaque, increasing free electron flow in an aqueous room temperature electride solution or combinations thereof.

24. The bioactive composition according to claim 1, whereby the electron transfer bridge is further complexed with at least one selected from the group consisting of chitosan, trehalose, ribose, glucose, cyclodextrin, or combinations thereof.

25. The bioactive composition according to claim 1, whereby the electron transfer bridge modulates electron flux and is further comprised of at least one selected from the group consisting of N-acetyl cysteine, coenzyme Q10, alpha lipoic acid, Omega-3 rich oil, or combinations thereof.

26. A bioactive composition operable to reduce triglycerides and total cholesterol comprised of at least one selected from the group consisting of vanillin, o-vanillin, fat-soluble vanillyl acylamides, or combinations thereof, and gallic acid, at least one selected from the group consisting of EDTA, cyclodextrin, CoQ10 encapsulated by cyclodextrin, lactoferrin or thermally stabilized lactoferrin, mixed tocopherols, mixed tocotrienols, or combinations thereof, and a protein fragment complex whereby the protein fragment complex is operable as an electron transfer bridge, and the electron transfer bridge is across the interface of an oil and water emulsion, wherein the electron transfer bridge contains between about 50 to 400 ppm of iron and the electron transfer bridge is an iron-sulfur cluster.

* * * * *